(12) United States Patent
Helfman et al.

(10) Patent No.: US 8,390,626 B2
(45) Date of Patent: Mar. 5, 2013

(54) RADIAL HISTOGRAMS FOR DEPICTING PATH INFORMATION

(75) Inventors: Jonathan I. Helfman, Half Moon Bay, CA (US); Joseph H. Goldberg, San Carlos, CA (US)

(73) Assignee: Oracle International Corporation, Redwood Shores, CA (US)

( * ) Notice: Subject to any disclaimer, the term of this patent is extended or adjusted under 35 U.S.C. 154(b) by 639 days.

(21) Appl. No.: 12/616,016

(22) Filed: Nov. 10, 2009

(65) Prior Publication Data

US 2010/0118032 A1 May 13, 2010

Related U.S. Application Data

(60) Provisional application No. 61/113,538, filed on Nov. 11, 2008.

(51) Int. Cl.
*G06T 11/20* (2006.01)
*G09G 5/00* (2006.01)
(52) U.S. Cl. ........................ 345/443; 345/690
(58) Field of Classification Search .................. 345/443
See application file for complete search history.

(56) References Cited

U.S. PATENT DOCUMENTS

| | | | | |
|---|---|---|---|---|
| 4,859,050 A | * | 8/1989 | Borah et al. ................ 351/210 |
| 4,973,149 A | * | 11/1990 | Hutchinson .................. 351/210 |
| 5,517,021 A | * | 5/1996 | Kaufman et al. ............. 250/221 |
| 5,649,061 A | * | 7/1997 | Smyth ........................... 706/16 |
| 5,726,916 A | * | 3/1998 | Smyth ........................... 702/151 |
| 6,381,339 B1 | * | 4/2002 | Brown et al. ................. 382/100 |
| 6,755,527 B1 | * | 6/2004 | Goldberg ..................... 351/209 |
| 7,136,073 B2 | * | 11/2006 | Newman ...................... 345/589 |
| 7,339,580 B2 | * | 3/2008 | Westerman et al. .......... 345/173 |
| 7,561,143 B1 | * | 7/2009 | Milekic ........................ 345/156 |
| 7,881,493 B1 | * | 2/2011 | Edwards et al. .............. 382/103 |
| 7,922,670 B2 | * | 4/2011 | Jones et al. .................. 600/558 |
| 2008/0222562 A1 | | 9/2008 | Helfman et al. |
| 2009/0043504 A1 | * | 2/2009 | Bandyopadhyay et al. .. 701/213 |
| 2010/0118030 A1 | | 5/2010 | Helfman et al. |
| 2010/0118267 A1 | | 5/2010 | Helfman et al. |
| 2010/0119111 A1 | | 5/2010 | Helfman et al. |
| 2010/0119112 A1 | | 5/2010 | Helfman et al. |
| 2010/0121812 A1 | | 5/2010 | Helfman et al. |

OTHER PUBLICATIONS

Torstling et al., The Mean Gaze Path: Information Reduction and Non-Intrusive Attention Detection for Eye Tracking, Master Thesis, Oct. 17, 2007, pp. 1-64.*
Duchowski, Eye-Based Interaction in Graphical Systems: Theory and Practice, Siggraph 2000, pp. I-1-I-25.*
Aula, A., et al., "Eye-tracking Reveals the Personal Styles for Search Result Evaluation," in Proceedings of Human-Computer Interaction, Tampere Unit for Computer-Human Interaction (TAUCHI), 2005, pp. 135-138, [Can also be found in Proceedings of INTERACT 2005, Int. Fed. Info Proc., pp. 1058-1061.].
Goldberg, J. H., et al., "Scanpath Clustering and Aggregation," Applications User Experience, Oracle USA, 8 pages, Proceedings of the Mar. 2010 Eye Tracking Research and Applications, ACM Press.
Goldberg, J. H., et al., "Visual Scanpath Representation," Applications User Experience, Oracle USA, 8 pages, Proceedings of the Mar. 2010 Eye Tracking Research and Applications, ACM Press.
U.S. Appl. No. 12/615,736, filed Nov. 10, 2009, Helfman et al.
U.S. Appl. No. 12/615,749, filed Nov. 10, 2009, Helfman et al.

(Continued)

*Primary Examiner* — M Good Johnson
(74) *Attorney, Agent, or Firm* — Kilpatrick Townsend & Stockton LLP

(57) ABSTRACT

Techniques for displaying path-related information. Techniques are provided for generating and displaying one or more graphical representations for a path. In one embodiment, a radial histogram is generated and output for a path.

20 Claims, 18 Drawing Sheets

OTHER PUBLICATIONS

U.S. Appl. No. 12/615,763, filed Nov. 10, 2009, Helfman et al.
U.S. Appl. No. 12/616,030, filed Nov. 10, 2009, Helfman et al.
U.S. Appl. No. 12/616,035, filed Nov. 10, 2009, Helfman et al.
Tobii Eye Tracking, "Tobii Eye Tracking: Research with Vision," 8 pages downloaded on Dec. 28, 2009 at URL: www.tobii.com.
Tobii Studio 2 brochure, "Comprehensive Eye Tracking analysis & visualization software," 5 pages downloaded on Dec. 28, 2009 at URL: www.tobii.com.
Tobii® Technology, "Tobii Studio™ Tobii Technology," Product Description, Revision 2.0, May 2009, pp. 1-26 downloaded on Dec. 28, 2009 at URL: www.tobii.com.
Tobii® Technology, "Tobii T/X series Eye Trackers," Product Description, Revision 2.0, May 2009, pp. 1-22 downloaded on Dec. 28, 2009 at URL: www.tobii.com.
Tobii T60 & T120 Eye Trackers, "Plug & Play Eye Trackers for On-Screen Research," 2 pages downloaded on Dec. 28, 2009 at URL: www.tobii.com.
Tobii T60 XL Eye Tracker, "Widescreen Eye Tracker for large stimulus display," 2 pages downloaded on Dec. 28, 2009 at URL: www.tobii.com.
Tobii X60 & X120 Eye Tracker, "Flexible Eye Trackers for Studies of Physical Objects," 2 pages downloaded on Dec. 28, 2009 at URL: www.tobii.com.
Aula, A., et al., "Eye-tracking Reveals the Personal Styles for Search Result Evaluation," in Proceedings of Human-Computer Interaction, pp. 135-138, Tampere Unit for Computer-Human Interaction (TAUCHI).
Aula, A., et al., "Multilingual Search Strategies," in Proceedings of CHI 2009—Spotlight on Works in Progress—Session 1, Boston, MA, USA, Apr. 4-9, 2009, pp. 3865-3870, ACM Press, Copyright 2009.
Beymer, D., et al., "WebGazeAnalyzer: A System for Capturing and Analyzing Web Reading Behavior Using Eye Gaze," in Proceedings of CHI 2005, Portland, Oregon, USA, Apr. 2-7, 2005, pp. 1913-1916, ACM Press, Copyright 2005.
Bednarik, R., et al., "Temporal Eye-Tracking Data: Evolution of Debugging Strategies with Multiple Representations," in proceedings of 2008 Symposium on Eye Tracking Research & Applications, Savannah, Georgia, Mar. 26-28, 2008, pp. 99-102, ACM Press, Copyright 2008.
Bojko, A., "Informative or Misleading? Heatmaps Deconstructed," J.A. Jacko (Ed.): Human-Computer Interaction, Part I, HCII 2009, LNCS 5610, 2009, pp. 30-39, Springer-Verlag Berlin Heidelberg.
Bojko, A., "Using Eye Tracking to Compare Web Page Designs: A Case Study," Journal of Usability Studies, May 2006, pp. 112-120, Issue 3, vol. 1.
Church, K., et al., "Dotplot: a Program for Exploring Self-Similarity in Millions of Lines of Text and Code," The Journal of Computational and Graphical Statistics, 1993, 12 pages (pp. 153-174 in publication), vol. 2, No. 2.
Cinar, M., "Eye Tracking Method to Compare the Usability of University Web Sites: A Case Study," M. Kurosu (Ed.): Human Centered Design, HCII 2009, LNCS 5619, 2009, pp. 671-678, Springer-Verlag Berlin Heidelberg.
Cutrell, E., et al., "What Are You Looking For? An Eye-tracking Study of Information Usage in Web Search," in Proceedings of CHI 2007, San Jose, California, USA, Apr. 28-May 3, 2007, 10 pages (pp. 407-416 in publication), ACM, Copyright 2007.
"Eyetools Eyetracking Research: But what does it all mean? Understanding eye-tracking results (Part 4)," Sep. 6, 2007, pp. 1-3, downloaded on Mar. 19, 2009 at URL: http://blog.eyetools.net/eyetools_research/2007/09/but-what-does-2.html.
Feusner, M., et al., "Testing for Statistically Significant Differences Between Groups of Scan Patterns," in Proceedings of 2008 Symposium on Eye Tracking Research & Applications, Savannah, Georgia, Mar. 26-28, 2008, pp. 43-46, ACM Press, Copyright 2008.
Goldberg, J. H., et al., "Computer Interface Evaluation Using Eye Movements: Methods and Constructs," International Journal of Industrial Ergonomics, 1999, pp. 631-645, vol. 24.
Goldberg, J. H., et al., "Eye Movement-Based Evaluation of the Computer Interface," Advances in Occupational Ergonomics and Safety, S. Kumar, (Ed.), 1998, pp. 529-532, IOS Press.
Goldberg, J. H., et al., "Eye Tracking in Web Search Tasks: Design Implications," in Proceedings of 2002 Symposium on Eye Tracking Research & Applications, ACM Press, 2002, 8 pages.
Goldberg, J. H., et al., "Scanpath Clustering and Aggregation," Applications User Experience, Oracle USA, 8 pages.
Goldberg, J. H., et al., "Visual Scanpath Representation," Applications User Experience, Oracle USA, 8 pages.
Granka, L., et al., "Incorporating Eyetracking into User Studies at Google," Workshop paper presented at CHI 2006, 2006, 2 pages, ACM Press.
Granka, L., et al., "Location Location Location: Viewing Patterns on WWW Pages," in Proceedings of the 2006 Symposium on Eye Tracking Research & Applications, San Diego, California, Mar. 27-29, 2006, p. 43, ACM Press, Copyright 2006.
Guan, Z., et al., "An Eye Tracking Study of the Effect of Target Rank on Web Search," in Proceedings of CHI 2007, San Jose, California, USA, Apr. 28-May 3, 2007, 4 pages (pp. 417-420 in publication), ACM Press, Copyright 2007.
Habuchi, Y., et al., "Comparison of Eye Movements in Searching for Easy-to-Find and Hard-to-Find Information in a Hierarchically Organized Information Structure," in Proceedings of the 2008 Symposium on Eye Tracking Research & Applications, Savannah, Georgia, Mar. 26-28, 2008, pp. 131-134, ACM Press, Copyright 2008.
Harris, R. L., "Information Graphics: A Comprehensive Illustrated Reference," 1999, pp. 164-177 and p. 191, Management Graphics, Atlanta, GA, Oxford University Press, New York, Copyright 1999.
Helfman, J. I., "Dotplot Patterns: A Literal Look at Pattern Languages," TAPOS, 2(1):31-41, 1995.
Helfman, J. I., "Similarity Patterns in Language," Proceedings of the IEEE Symposium on Visual Language, 1994, 3 pages (pp. 173-175 in publication), IEEE Press.
Hembrooke, H., et al., "Averaging Scan Patterns and What They Can Tell Us," in Proceedings of the 2006 symposium on Eye Tracking Research & Applications, San Diego, California, Mar. 27-29, 2006, p. 41, ACM Press, Copyright 2006.
Heminghous, J., et al., "iComp: A Tool for Scanpath Visualization and Comparison," in Proceedings of the 2006 Applied Perception in Graphics and Visualization, Boston, Massachusetts, Jul. 28-29, 2006, p. 152, ACM Press, Copyright 2006.
Hornof, A. J., "Cognitive Strategies and Eye Movements for Searching Hierarchical Computer Displays," Paper: Modeling User Behavior, in Proceedings of CHI 2003, Ft. Lauderdale, Florida, USA, Apr. 5-10, 2003, pp. 249-256, CHI 2003: New Horizons, vol. No. 5, Issue No. 1, ACM Press, Copyright 2003.
Huang, Y., et al., "Rapid and Sensitive Dot-matrix Methods for Genome Analysis," Bioinformatics Advance Access, Jan. 22, 2004, pp. 460-466, vol. 20, No. 4, Oxford University Press, Copyright 2004, downloaded on Mar. 15, 2010 from URL : http://bioinformatics.oxfordjournals.org.
Josephson, S., et al., "Visual Attention to Repeated Internet Images: Testing the Scanpath Theory on the World Wide Web," in Proceedings of the 2002 Symposium on Eye Tracking Research & Applications, New Orleans, Louisiana, USA, pp. 43-49, ACM Press, Copyright 2002.
Levenshtein, V. I., "Binary Codes Capable of Correcting Deletions, Insertions, and Reversals," Cybernetics and Control Theory, Doklady Physics, Feb. 1966, pp. 707-710, vol. 10, No. 8.
Lorigo, L., et al., "Eye Tracking and Online Search: Lessons Learned and Challenges Ahead," Journal of the American Society for Information Science and Technology, 2008, pp. 1041-1052, vol. 59, No. 7, Copyright 2008.
Mankowski, W. C., et al., "Finding Canonical Behaviors in User Protocols," in Proceedings of CHI 2009, Boston, MA, USA, Apr. 4-9, 2009, 4 pages, ACM Press, Copyright 2009.
Marshall, S. P., "Identifying Cognitive State from Eye Metrics," Aviation, Space, and Environmental Medicine, May 2007, pp. B165-B186, vol. 78, No. 5, Section II.
Matsuda, Y., et al., "An Analysis of Eye Movements During Browsing Multiple Search Results Pages," J.A. Jacko (Ed.): Human-Computer Interaction, Part I, HCII, LNCS 5610, pp. 121-130, Copyright 2009 Springer-Verlag Berlin Heidelberg, Copyright 2009.

Myers, C. W., "Toward a Method of Objectively Determining Scanpath Similarity," [Abstract], Journal of Vision, Sep. 23, 2005, 2 pages, vol. 5, No. 8, Abstract 693, downloaded on Jan. 5, 2010 from URL: http://www.journalofvision.org/5/8/693/.

Najemnik, J., et al., "Optimal Eye Movement Strategies in Visual Search," Nature, Mar. 17, 2005, pp. 387-391, vol. 434, Copyright 2005 Nature Publishing Group.

Raiha, K., et al., "Static Visualization of Temporal Eye-Tracking Data," M.F. Costabile and F. Paterno (Eds.): INTERACT 2005, LNCS 3585, 2005, pp. 946-949, Copyright IFIP International Federation for Information Processing 2005.

Rantala, H., "Eye2i: Coordinated Multiple Views for Gaze Data," in Proceedings of the 2008 Symposium on Eye Tracking Research & Applications, Savannah, Georgia, Mar. 26-28, 2008, pp. 147-148, ACM Press, Copyright 2008.

Salvucci, D. D., et al., "Identifying Fixations and Saccades in Eye-Tracking Protocols," in Proceedings of the 2000 Symposium on Eye Tracking Research & Applications, Palm Beach Gardens, FL, USA, pp. 71-78, ACM Press, Copyright 2000.

Santella, A., et al., "Robust Clustering of Eye Movement Recordings for Quantification of Visual Interest," in Proceedings of the 2004 Symposium on Eye Tracking Research & Applications, San Antonio, Texas, 2004, pp. 27-34, ACM Press, Copyright 2004.

Smith, T. F., et al., "Identification of Common Molecular Subsequences," Reprinted from Journal of Molecular Biology, 1981, pp. 195-197, vol. 147, Academic Press, Copyright 1980.

Tufte, E. R., "Beautiful Evidence," Sparklines: Intense Word-Sized Graphics, Graphic Press LLC, Cheshire, CT., pp. 46-63, Copyright 2006.

Tufte, E. R., "The Visual Display of Quantitative Information," Theory of Data Graphics, Graphic Press LLC, Cheshire, CT., pp. 170-175, Copyright 1983.

Uwano, H., et al., "Analyzing Individual Performance of Source Code Review Using Reviewers' Eye Movement," in Proceedings of 2006 Eye Tracking Research & Applications, San Diego, California, Mar. 27-29, pp. 133-140, ACM Press.

Wattenberg, M., "Arc Diagrams: Visualizing Structure in Strings," in Proceedings of the IEEE Symposium on Information Visualization (InfoVis'02), 2002, 8 pages, IEEE Computer Society.

Werman, M., et al., "A Bayesian Method for Fitting Parametric and Nonparametric Models to Noisy Data," IEEE Transactions on Pattern Analysis and Machine Intelligence, May 2001, pp. 528-534, vol. 23, No. 5, Copyright 2001.

West, J. M., et al., "EyePatterns: Software for Identifying Patterns and Similarities Across Fixation Sequences," in Proceedings of the 2006 Symposium on Eye Tracking Research & Applications, San Diego, California, Mar. 27-29, 2006, pp. 149-154, ACM Press, Copyright 2006.

Wooding, D. S., "Eye Movements of Large Populations: II. Deriving Regions of Interest, Coverage, and Similarity Using Fixation Maps," Behavior Research Methods, Instruments, & Computers, 2002, pp. 518-528, vol. 34, No. 4, Psychonomic Society, Inc., Copyright 2002.

U.S. Appl. No. 12/615,736, filed Nov. 10, 2009, Office Action mailed May 24, 2012, 4 pages.

U.S. Appl. No. 12/616,030, filed Nov. 10, 2009, Office Action mailed Jul. 20, 2012, 11 pages.

U.S. Appl. No. 12/616,035, filed Nov. 10, 2009, Office Action mailed Jul. 23, 2012, 10 pages.

* cited by examiner

RADIAL HISTOGRAMS FOR DEPICTING PATH INFORMATION

CROSS-REFERENCES TO RELATED APPLICATIONS

The present application claims benefit under 35 USC 119 (e) of U.S. Provisional Application No. 61/113,538, filed on Nov. 11, 2008, entitled "Techniques For Analyzing Paths," the entire contents of which are incorporated herein by reference for all purposes.

This application herein incorporates by reference for all purposes the entire contents of the following applications:

(1) U.S. Non-Provisional application Ser. No. 12/616,030 titled "RADIAL VECTOR PLOTS FOR PATHS" filed concurrently with the present application; and (2) U.S. Non-Provisional application Ser. No. 12/616,035 titled "GRAPHICAL REPRESENTATIONS FOR AGGREGATED PATHS" filed concurrently with the present application.

BACKGROUND

Embodiments of the present invention relate to displaying information related to paths, and more specifically to techniques for displaying graphical representations for a path.

Analysis of paths is performed in various different fields or domains. For example, in eyetracking analysis, scanpaths representing users' eye movements while viewing a scene may be analyzed to determine high-level scanning strategies. The scanning strategies determined from such an analysis may be used to improve product designs. For example, by studying scanpaths for users viewing a web page, common viewing trends may be determined and used to improve the web page layout. Various other types of analyses on paths may be performed in other fields. Accordingly, new and improved techniques for displaying path-related information that can provide insight into characteristics of the path and that facilitate comparisons of paths are always desirable.

BRIEF SUMMARY

Embodiments of the present invention provide techniques for displaying path-related information. Techniques are provided for generating and displaying one or more graphical representations for a path. In one embodiment, a radial histogram is generated and output for a path.

In one embodiment, techniques are provided for displaying a graphical representation for a path. A set of angles associated with the path may be determined. The angles in the set of angles are then grouped into a set of one or more groups. A value is determined for each group in the set of groups, based upon the angles from the set of angles that are grouped in that group. A graphical representation is then output for the path. The graphical representation may comprise a bar for each non-empty group in the set of groups. The length of a bar for a group has a length based upon the value determined for the group and the bar is rotated by an angle representative of the group. In one embodiment, the value determined for each group in the set of groups is indicative of a number of angles from the set of angles that are grouped in that group.

Different techniques may be used for determining angles in the set of angles associated with the path. In one embodiment, the path comprises one or more path segments and an angle each path segment makes with respect to a common absolute reference is determined. In another embodiment, for each pair of adjoining path segments in the path, an angle between the path segments in the pair is determined.

In one embodiment, a second graphical representation representing an aggregate vector may be rendered for a path. In one such embodiment, an average magnitude is determined that is equal to the average of the values determined for one or more non-empty groups in the set of groups. An average angle is determined that is equal to the average of the angles representative of the one or more groups in the set of groups. A second graphical representation is then output based upon the aggregate magnitude and the aggregate angle. In another embodiment, for each non-empty group in the set of groups, a first orthogonal and a second orthogonal are determined for the group based upon the value determined for the group and the angle representative of the group. An aggregate magnitude is then determined based upon the first and second orthogonals determined for the set of groups. An aggregate angle is determined based upon the first and second orthogonals determined for the set of groups. A second graphical representation is then rendered based upon the aggregate magnitude and the aggregate angle.

In one embodiment, in order to generate the graphical representation, for each non-empty group in the set of groups, a length for the bar for the group is determined based upon the value determined for the group and an angle representative of the group. The lengths of the bars may then be scaled based upon an area available for outputting the graphical representation. The scaled bars are then displayed as part of the graphical representation.

In one embodiment, the path for which the various graphical representations are output is a scanpath representing a path followed by an eye when viewing a scene.

The foregoing, together with other features and embodiments will become more apparent when referring to the following specification, claims, and accompanying drawings.

BRIEF DESCRIPTION OF THE DRAWINGS

In order to more fully understand the present invention, reference is made to the accompanying drawings with the understanding that these drawings are not intended to limit the scope of the claimed invention.

DETAILED DESCRIPTION

In the following description, for the purposes of explanation, specific details are set forth in order to provide a thorough understanding of the embodiments of the invention. However, it will be apparent that the invention may be practiced without these specific details.

Embodiments of the present invention provide techniques for displaying path-related information. Techniques are provided for generating and displaying graphical representations for one or more paths.

A path may be defined as a sequence of two or more points. The first point in the sequence of points may be referred to as the start point of the path and the last point in the sequence may be referred to as the end point of the path. The portion of a path between any two consecutive points in the sequence of points may be referred to as a path segment. A path may comprise one or more segments.

There are different types of paths. Examples described below have been described with reference to a specific type of path, referred to as a scanpath, which is used to track eye movements. A scanpath is a path that an eye follows when viewing a scene. A scanpath is defined by a sequence of fixation points (or gaze locations). A path segment between two consecutive fixation points in the sequence of fixation points is referred to as a saccade. A scanpath is thus a sequence of fixation points connected by saccades during scene viewing where the saccades represent eye movements between fixation points. For purposes of simplicity, the scanpaths described below are 1- or 2-dimensional paths. The teachings of the present invention may however also be applied to paths in multiple dimensions.

While embodiments of the present invention have been described in the context of scanpaths, this is not intended to limit the scope of the present invention as recited in the claims to scanpaths. Teachings of the present invention may also be applied to other types of paths occurring in various different domains such as a stock price graph, a path followed by a car between a start and an end destination, and the like.

Figure 1:
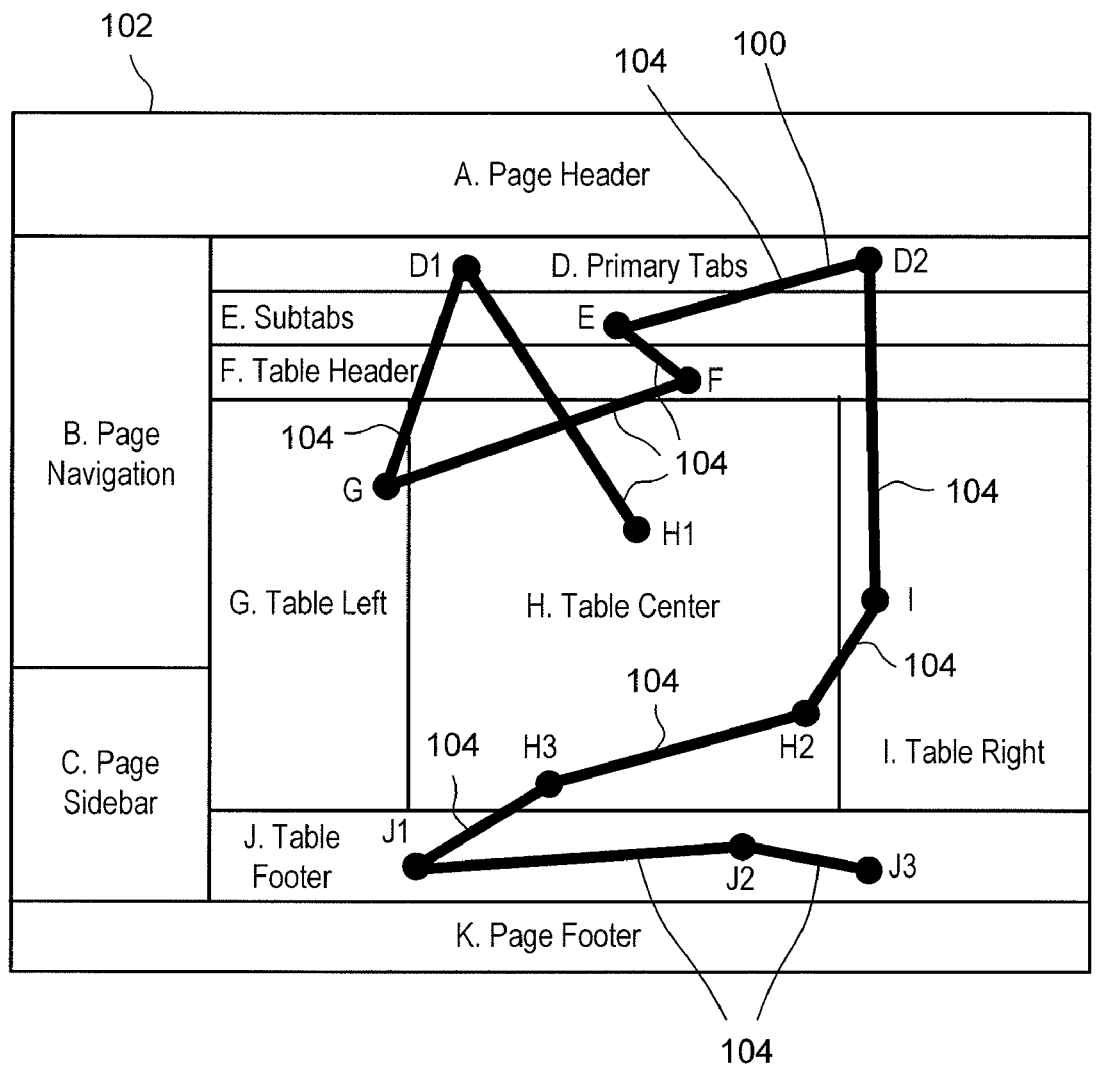
FIG. 1 depicts an example of a scanpath representing a user's eye movements while viewing a webpage.

The scenes that are viewed by a user for generating scanpath data may be of various types. FIG. 1 depicts an example of a scanpath 100 representing a user's eye movements while viewing a webpage 102. Webpage 102 may be displayed on an output device such as a monitor and viewed by the user. As shown in FIG. 1, webpage 102 may be considered to comprise multiple regions such as: A (page header), B (page navigation area), C (page sidebar), D (primary tabs area), E (subtabs area), F (table header), G (table left), H (table center), I (table right), J (table footer), and K (page footer). Path 100 shows the user eye movements across the various regions of page 102. The circles depicted in FIG. 1 represent fixation points. A fixation point marks a location in the scene where the saccadic eye movement stops for a brief period of time while viewing the scene. Scanpath 100 depicted in FIG. 1 is defined by the following sequence of fixation points {H1, D1, G, F, E, D2, I, H2, H3, J1, J2, J3} where H1 represents the start point for the scanpath and J3 represents the end point of the path. Path 100 comprises several path segments (or saccades) 104 connecting the fixation points.

In one embodiment, information regarding the fixation points and saccadic eye movements between the fixation points may be gathered using eye tracking devices such as devices provided by Tobii (e.g., Tobii T60 eye tracker). An eye-tracking device such as the Tobii T60 eye tracker is capable of capturing information related to the saccadic eye activity including location of fixation points, fixation durations, and other data related to viewing a scene. The Tobii T60 uses infrared light sources and cameras to gather information about the user's eye movements while viewing a scene.

The scanpath data gathered by an eye tracker is used by embodiments of the present invention to generate one or more graphical representations for the scanpath. In one embodiment, a radial histogram is generated and output for the scanpath based upon the scanpath data. In another embodiment, a radial vector plot is generated and output based upon scanpath data collected for the scanpath. In another embodiment, a graphical representation in the form of an aggregate vector may be generated and output. In yet other embodiment, a graphical representation may be generated for an aggregation of multiple paths.

As described below in further detail, each graphical representation identified above is generated based upon one or more characteristics of the path such as angles associated with the path, length of path segments in the path, etc. As a result, a graphical representation generated for a path provides a graphical signature for the path. Graphical representations generated for different paths may then be used to compare the paths. The graphical representations thus serve as tools that may be used to analyze and compare paths. For example, the graphical representations generated for a scanpath may provide an indication of the directionality (both absolute and relative) of the scan, the length of saccades, and the like. The graphical representations generated for multiple scanpaths maybe used to compare the scanpaths.

Figure 2:
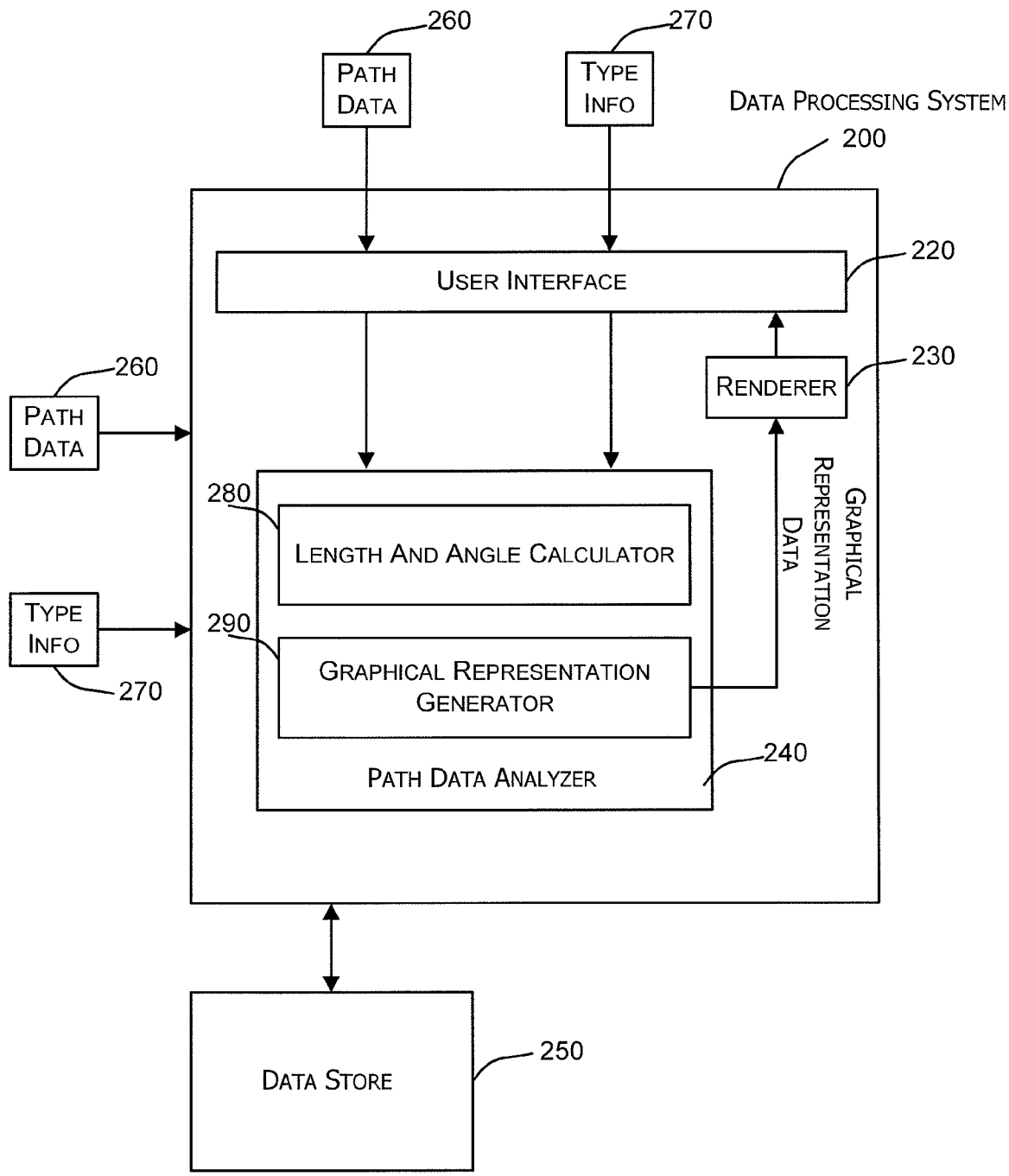
FIG. 2 is a simplified logical diagram of a data processing system configured to generate graphical representations according to an embodiment of the present invention.

FIG. 2 is a simplified logical diagram of a data processing system 200 configured to generate graphical representations according to an embodiment of the present invention. As depicted in FIG. 2, data processing system 200 comprises several components including a user interface 220, a renderer 230, and a path data analyzer 240. The various components may be implemented in hardware, or software (e.g., code, instructions, program executed by a processor), or combinations thereof. Data processing system 200 may be coupled to a data store 250 that is configured to store data related to processing performed by system 200. For example, path data (e.g., scanpath data) may be stored in data store 250.

User interface 220 provides an interface for receiving information from a user of data processing system 200 and for outputting information from data processing system 200. For example, a user of data processing system 200 may enter path data 260 for a path to be analyzed via user interface 220. Type information 270 may also be provided via user interface 220. Type information 270 may identify a specific type(s) of graphical representation to be generated using path data 260. System 200 may also receive path data 260 and type information 270 via other interfaces such as from an eye tracking device or some other device, over the network, etc.

Path data 260 received by system 200 comprises data related to a path for which a graphical representation is to be generated by system 200. Path data 260 for a path may comprise information identifying a sequence of points included in the path, and other path related information. For example, for a scanpath, path data 260 may comprise information related to a sequence of fixation points defining the scanpath. Path data 260 may optionally include other information related to a scanpath such as the duration of each fixation point, inter-fixation angles, inter-fixation distances, etc.

System 200 may receive path data 260 from various sources. As described above, a user may provide the path data via user interface 220. The path data may also be received from other sources such as from an eye tracker device. The path data may be received in various formats. In one embodiment, the path data received by system 200 may be stored in data store 250 for further processing.

Path data analyzer 240 is configured to process the path data and generate one or more graphical representations for the path represented by the path data. According to an embodiment of the present invention, different types of graphical representations may be generated by path data analyzer 240 for a path including different types of radial histograms, radial vector plots, aggregate vectors, and the like. Information identifying the type(s) of graphical representation to be generated may be provided via type information 270.

In one embodiment, the graphical representations are based upon angles associated with a path. There are different ways in which an angle associated with a path may be calculated. In one embodiment, path segments in a path may be used to determine a set of angles associated with the path. According to one technique, the set of angles associated with a path may include angles made by path segments of the path measured relative to an absolute reference. This technique of measuring angles for a path is referred to as an "absolute angle" technique. In this technique, the direction of the absolute reference may be preconfigured. In one embodiment, the positive X axis or a reference along 3:00 in a clock is used as the reference and angles are measured in a counter-clockwise direction from the reference.

According to another technique, the set of angles associated with a path may include angles made by adjoining path segments in a path measured relative to each other. For each pair of adjoining path segments, an angle between the two path segments is measured and included in the set of angles for the path. This technique of measuring angles for a path is referred to as a "relative angle" technique. A graphical representation may be generated based either using the absolute angle or the relative angle technique. Information identifying the type of angle measuring technique to be used for generating a graphical representation may be specified in type information 270. If no technique is specified, then a preconfigured default technique (e.g., the absolute angle technique) may be used.

In the embodiment depicted in FIG. 2, path data analyzer 240 comprises a length and angle calculator component 280 and a graphical representation generator 290. These components may be implemented in hardware, or software, or combination thereof. In one embodiment, length and angle calculator 280 is configured to analyze path data 260 to determine the lengths of the path segments in the path being analyzed and angles (either absolute or relative) associated with the path. In one embodiment, path data analyzer 240 is configured to determine the length and angles information for a path based upon path data 260. Length and angle calculator 280 may then forward the determined information to graphical representation generator 290 for further processing.

Graphical representation generator 290 is configured to generate a graphical representation for the path based upon information received from length and angle calculator 280. Examples of graphical representations generated by generator 290 include a radial histogram based upon absolute angles, a radial histogram based upon relative angles, a radial vector plot based upon absolute angles, a radial vector plot based upon relative angles, aggregate vectors, and graphical representations for aggregated paths. Information encoding the graphical representation(s) generated by graphical representation generator 290 may then be provided to renderer 230 that is configured to render the graphical representation via user interface 220. For example, the rendered graphical representation may be displayed on a screen of an output device or written as image data into a file. Information encoding the generated graphical representation may also be stored in data store 250.

As described above, embodiments of the present invention are capable of generating different kinds of graphical representations. The following sections provide further details for the various graphical representations including techniques used for generating the representations.

Radial Histograms

A radial histogram is a type of histogram. A histogram provides a way to summarize the distribution of values in a dataset or input sequence by counting occurrences of the values. A histogram provides a count of the members of each subset of a dataset or input sequence.

There are various ways in which values in a data set or input sequence may be grouped into subsets. In one embodiment, a grouping function may be used to create the subsets. The grouping function defines a way for partitioning the dataset into subsets such that each value in the dataset lies in only one subset. The subsets thus do not overlap. For example, using an equality function as the grouping function: if two values in the dataset are equal, then they are grouped together and form one subset; if two values are not equal, then they are distinct and are grouped into separate groups or subsets.

For example, for the dataset {1, 2, 1, 3, 4, 1, 2}, using an equality function as the grouping function, the following groupings and associated counts are generated: {{value=1, count: 3}, {value=2; count 2}, {value=3, count: 1}, {value=4, count: 1}}. The count associated with a group or subset indicates the number of members of the dataset that are grouped in that group. A histogram may then be generated for the dataset. Each group or subset is represented in the histogram by a bar with the length of the bar corresponding to the count of the values for that group or subset.

The equality function described above is just an example of a grouping function that may be used. Other grouping functions may be used in other applications. For example, when only a rough sense of distribution of values in a very large dataset is required, it may be impractical to count every single distinct value. A less precise grouping function may be used in such circumstances. Whenever grouping functions use a form of matching other than strict equality, there is a reduction in data precision, but many times this reduction in precision is desired. In the case of eye-tracking data, which is considered to be inherently noisy, a binning function is used as the grouping function. The binning function reduces precision and thus promotes matching of noisy data to better help comparisons of the noisy data.

Using a binning function, the range of input values (the difference between the maximum possible value and the minimum possible value in the input dataset, plus one) is divided into equal-sized, non-overlapping sub-ranges or groups called "bins." The bins form a partition of the dataset values. When using binning as a grouping function, the histogram is based upon the count of the values in each bin. For example, for the dataset {1, 2, 1, 3, 4, 1, 2}, the range of the dataset is (max−min+1)=4−1+1=4. If the range is divided into two bins "1-2" and "3-4", then the bins and their associated counts are as follows: {{value: "1-2", count: 5, {value: "3-4", count: 2}}. Binning is used to create histograms for very large datasets, which may have a large range, and a large number of distinct values.

In one embodiment, a binning function is used to generate graphical representations for a path such as a scanpath. In one such embodiment, the input dataset to the binning function is a set of angles associated with the path for which a graphical representation is to be generated. For example, a set of angles associated with a scanpath may be determined and provided as input to a binning function.

The binning function is then used to partition the set of angles associated with a scanpath. Different bins may be used. For example, in one embodiment the following 4 non-overlapping bins may be used (assuming the angle precision is measured in integers): {{0° to 89°}, {90° to 179°}, {180° to 269°}, {270° to 359°}}. For the example input sequence of angles {120, 24, 93, 326, 42, 266, 335, 182}, the binning function results in the following bins and associated counts being determined: {{value: "0 to 89", count: 2}, {value: "90 to 179", count: 2}, {value: "180 to 269", count: 2}, {value: "270 to 359", value: 2}}.

Generally, when an angle is measured, the angle precision is not typically measured in integers, but rather calculated as a fractional value with arbitrary precision. Binning, in the typical case, is used to reduce precision to match angles that are 'close' to each other, where 'closeness' is determined by the range of angles in each bin. It is more precise, therefore, to indicate the above bins like this: {{0° to <90°}, {90° to <180°}, {180° to <270°}, {270° to <360°}} (where <90° indicates less than 90°, etc.). For purposes of descriptive simplicity, however, it may be assumed that angle precision is measured in integers.

A radial histogram may then be generated for the path based upon the results of the binning. In one embodiment, the radial histogram comprises a bar for each bin or group that has a non-zero count and the length or height of the bar for a bin or group is proportional to the count for that bin or group. Further, in a radial histogram, the bars corresponding to the bins or groups are positioned such that the center-points of the bottom edges of the bars are the same and the bars are rotated about the center-point of their bottom edges by a particular angle. Each bar in the radial histogram is rotated by an angle that is representative of the bin that the bar represents. There are multiple ways that an angle may be chosen to represent a bin. The angle of rotation for the bars in a radial histogram may be different in different embodiments so long as the angles associated with the bars are indicative of the bins or groups represented by the bars.

For example, in one embodiment, bars may be rotated by the average of the bin's angular range. In such an embodiment, a bar representing a bin with angle range 0° to <90° may be rotated by 45°, a bar representing a bin with angle range 90° to <180° may be rotated by 135°, a bar representing a bin with angle range 180° to <270° may be rotated by 225°, and a bar representing a bin with angle range 270° to <360° may be rotated by 315°. In another embodiment, bars may be rotated by the minimum angle of the range of angles in the bin. In such an embodiment, a bar representing a bin with angle range 0° to <90° may be rotated by 0°, a bar representing a bin with angle range 90° to <180° may be rotated by 90°, a bar representing a bin with angle range 180° to <270° may be rotated by 180°, and a bar representing a bin with angle range 270° to <360° may be rotated by 270°. In yet another embodiment, bars may be rotated by the average of the actual path angles that lie within the bin's angle range. Other angles may be used to represent bins in alternative embodiments. Because the bars in a radial histogram are positioned by rotating them about their center-points of their bottom edges by a corresponding angle, radial histograms are particularly suited to datasets that comprise angles such as datasets for paths.

Figure 3:
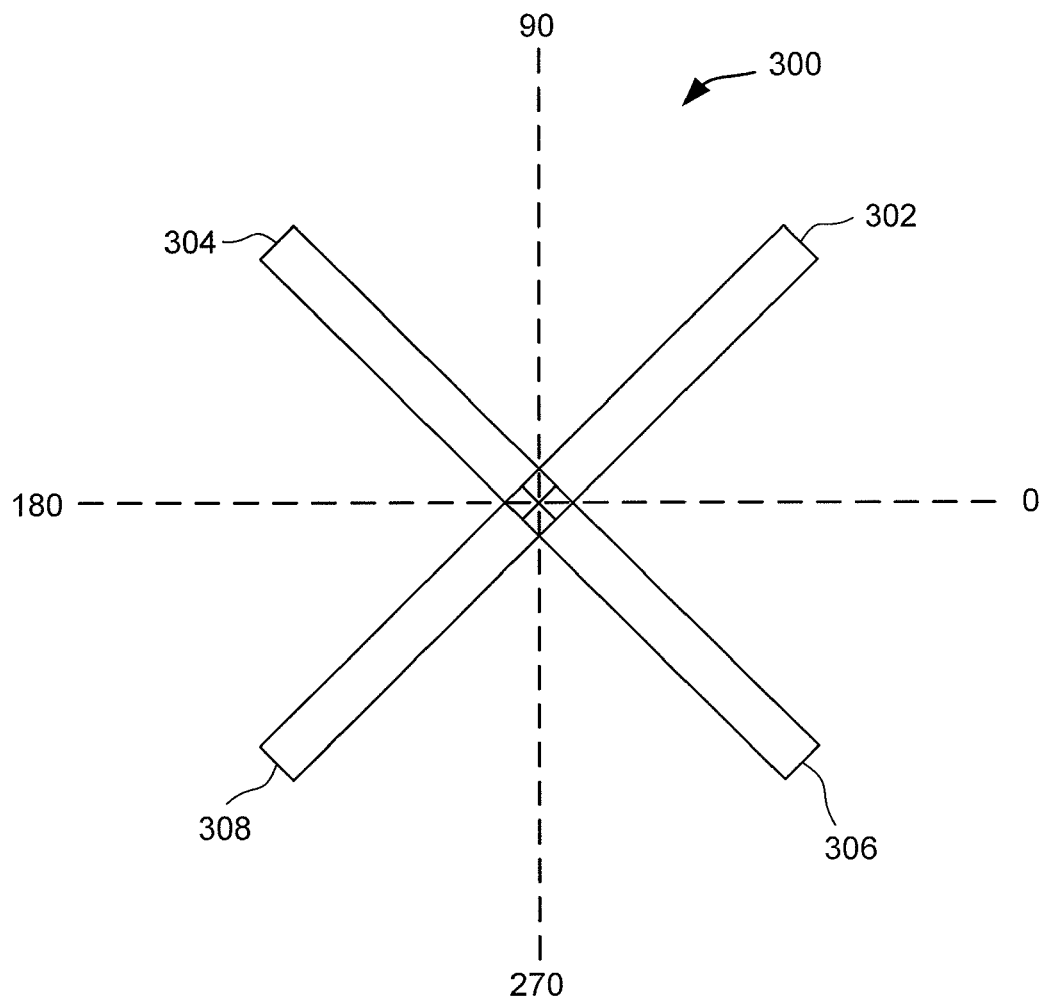
FIG. 3 depicts an example of a radial histogram that may be generated and displayed according to an embodiment of the present invention.

FIG. 3 depicts an example of a radial histogram 300 that may be generated and displayed according to an embodiment of the present invention. Radial histogram 300 is generated for the input angles sequence {120, 24, 93, 326, 42, 266, 335, 182} using bins {{0° to <90°}, {90° to <180°}, {180° to <270°}, {270° to <360°}} resulting in the following partitioning of the input sequence: {{value: "0 to <90", count: 2}, {value: "90 to <180", count: 2}, {value: "180 to <270", count: 2}, {value: "270 to <360", value: 2}}. The input angles may have been measured using an absolute angle technique or a relative angle technique. In FIG. 3, bar 302 represents bin {0° to <90°} and is rotated by 45° in the radial histogram, bar 304 represents bin {90° to <180°} and is rotated by 135°, bar 306 represents bin {180° to <270°} and is rotated by −45°, and bar 308 represents bin {270° to <360°} and is rotated by −135°. The lengths of the bars are the same since the counts associated with the bins or groups is the same.

For radial histogram 300 depicted in FIG. 3, zero degrees is to the right (3:00 on a clock). Positive angles are plotted counter-clockwise. In alternative embodiments, zero degrees may be in some other direction (e.g., at 12:00 on a clock) and the angles may be plotted differently such as using a clockwise direction for positive angles. Further, as indicated above, the angle at which a bar representing a bin is drawn may be different in alternative embodiments. For example, instead of positioning bar 302 representing the bin "0-90" at a 45° angle, the bar could have been drawn at 0° or at 90°, etc., so long as the other bars are drawn using the same convention.

Figure 4:
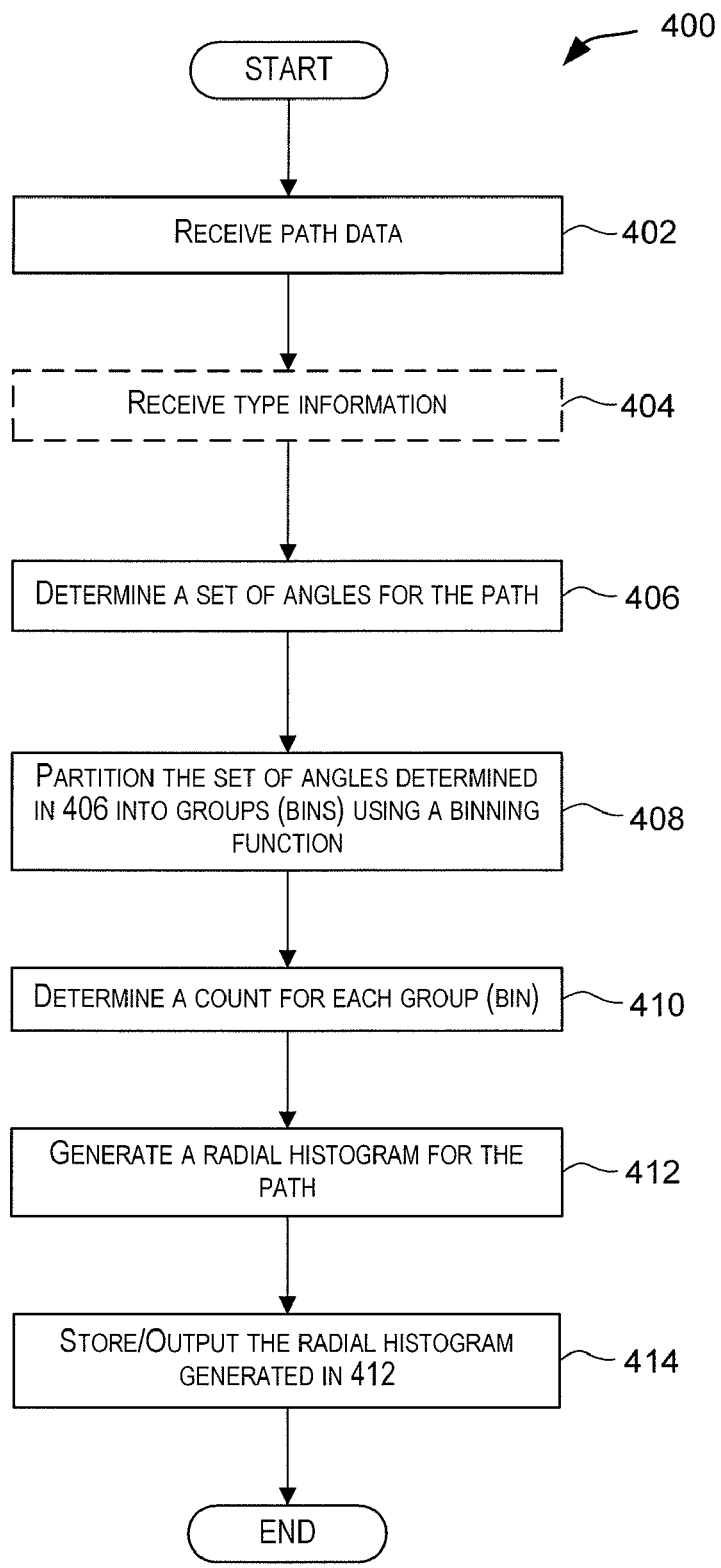
FIG. 4 depicts a high level simplified flowchart depicting a method for generating a radial histogram according to an embodiment of the present invention.

FIG. 4 depicts a high level simplified flowchart 400 depicting a method for generating a radial histogram according to an embodiment of the present invention. The method depicted in FIG. 4 may be performed by software (e.g., code, program, and instructions) executed by a processor, in hardware, or combinations thereof. The software may be stored on a computer-readable storage medium. In one embodiment, the method may be performed by path data analyzer 240 depicted in FIG. 2. The method depicted in FIG. 4 is not intended to limit the scope of the application as recited in the claims.

As depicted in FIG. 4, path data for a path for which a radial histogram is to be generated is received (step 402). For example, path data may be received for a scanpath tracking a user's eye movements while viewing a scene. The path data may be received from various sources including from a user via user interface 220, from a device such as an eye tracker, or from another source. In one embodiment, the path data may be stored and retrieved from data store 250. The path data may be received in different formats. For example, the data may be received as data comprising fixation points, transitions between fixation points, etc.

Type information may optionally be received (step 404). The information received in 404 may indicate whether absolute angles or relative angles are to be used for generating the radial histogram. If no type information is received, then a default method (e.g., using absolute angles) may be used to generate the radial histogram.

The path data received in 402 is then analyzed to determine a set of angles associated with the path (step 406). The angles may be measured using either the absolute angle method or the relative angles method, based upon the type information received in 404. For example, if the information received in 404 indicates that a radial histogram based upon relative angles is to be generated, then relative angles may be determined in 406; else, absolute angles may be determined for the path in 406.

In one embodiment, the angles associated with a path are determined based upon the path segments that make up that path. There are various different ways for calculating angles for a path. In one embodiment, the angles for a path may be measured using two different methods: (1) absolute angle method; or (2) relative angle method. Using the absolute angle method, for each path segment of a path, an angle that the path segment makes with an absolute reference is measured and included in the set of angles for the path. Accordingly, using the absolute angle method, the number of angles in the set of angles for a path is equal to the number of path segments in the path. In one embodiment, the positive X axis or a reference along 3:00 in a clock is used as the reference and angles are measured in a counter-clockwise direction from the reference. Other absolute references and ways of measuring the angles may be used in alternative embodiments.

Figure 5A:
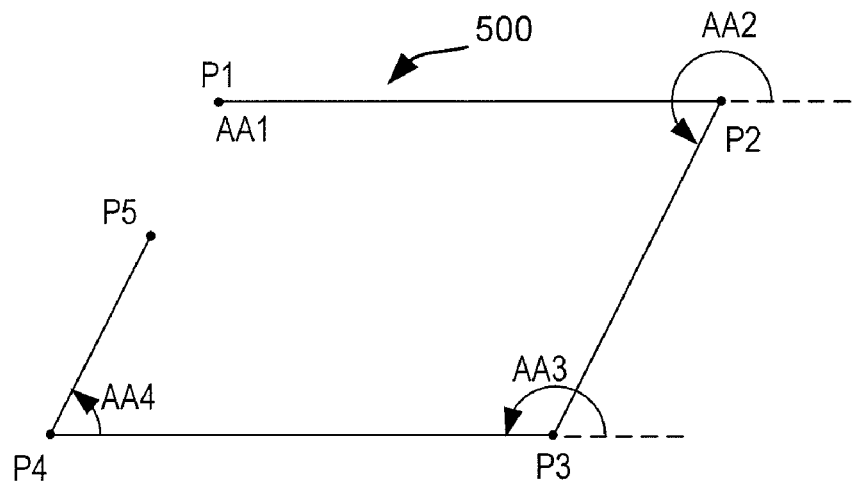
FIG. 5A depicts a sample path and absolute angles that may be calculated for the path according to an embodiment of the present invention.

FIG. 5A depicts a sample path 500 and absolute angles that may be calculated for the path according to an embodiment of the present invention. Path 500 is defined by the sequence of points {P1, P2, P3, P4, P5}, with P1 being the start point and P5 being the end point. Points P1, P2, P3, P4, and P5 may, for example, represent fixation points defining a scanpath. Path 500 has four path segments P1P2, P2P3, P3P4, and P4P5. In FIG. 5A the reference used for calculating the absolute angles is the positive X axis (along 3:00 in the clock). The absolute angles calculated for path 500 are AA1 (angle between path segment P1P2 and the reference, equal to zero degrees), AA2 (angle between path segment P2P3 and the reference), AA3 (angle between path segment P3P4 and the reference), and AA4 (angle between path segment P4P5 and the absolute). Accordingly, the set of absolute angles for path 500 is {AA1, AA2, AA3, AA4}.

Using the relative angles method, the set of angles for a path include angles between adjoining path segments of the path. In one embodiment, for each path segment, an angle that the path segment makes relative to the adjoining path segment is measured and included in the set of relative angles for the path. Since a relative angle is measured relative to two adjoining paths, the number of relative angles for a path is one less than the total path segments for the path.

Figure 5B:
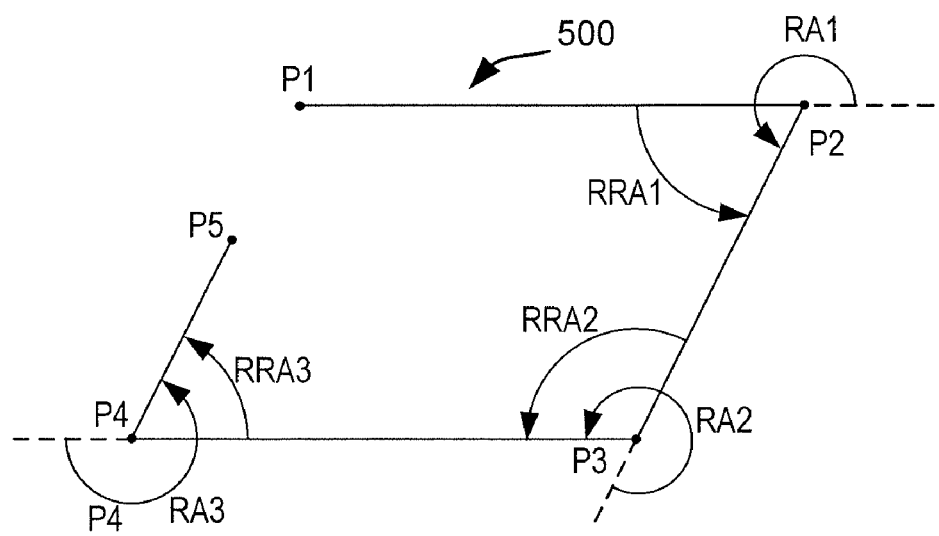
FIG. 5B depicts a sample path and relative angles calculated for the path according to an embodiment of the present invention.

FIG. 5B depicts relative angles calculated for path 500 according to an embodiment of the present invention. The relative angles calculated for path 500 are RA1, (relative angle between path segment P1P2 and P2P3), RA2 (relative angle between path segment P2P3 and P3P4), and RA3 (relative angle between path segment P3P4 and P4P5). Accordingly, a set of relative angles for path 500 is {RA1, RA2, RA3}.

There are different ways in which a relative angle may be determined between two adjoining path segments. The method depicted in FIG. 5B is one such way. Other ways may be used in alternative embodiments. For example, in one embodiment, angles RRA1, RRA2, and RRA3 may represent the set of relative angles for path 500.

Referring back to FIG. 4, the set of angles determined in 406 is then partitioned into groups (or bins) using a binning or grouping function (step 408). Various different binning functions may be used. For example, as described above, the data may be partitioned using the four groups (bins): {{0° to <90°}, {90° to <180°}, {180° to <270°}, {270° to <360°}}. Using the absolute angles example depicted in FIG. 5A, the angles would be binned as follows:

AA1=0°→{0° to <90°} group
AA2=between 180° and 270°→{180° to <270°} group
AA3=180°→{180° to <270°} group
AA4=between 0° and <90°→{0° to <90°} group Using relative angles RA1, RA2, and RA3 depicted in FIG. 5B, the angles would be binned as follows:
RA1=between 180° and <270°→{180° to <270°} group
RA2=between 270° and <360°→{270° to <360°} group
RA3=between 180° and <270°→{180° to <270°} group After the input angles have been partitioned in 408, a count is determined for each group (bin) (step 410). The count for a group (bin) identifies that number of angles that are grouped in that group (bin). The groups and respective counts for path 500 depicted in FIG. 5A using absolute angles would be as follows: {{value: "0° to <90°", count: 2}, {value: "90° to <180°", count: 0}, {value: "180° to <270°", count: 2}, {value: "270° to <360°", count: 0}}. Using relative angles RA1, RA2, and RA3 depicted FIG. 5B, the bins and associated counts would be: {{value: "0° to <90°", count: 0}, {value: "90° to <180°", count: 0}, {value: "180° to <270°", count: 2}, {value: "270° to <360°", count: 1}}.

A radial histogram is then generated for the path (step 412). In one embodiment, the radial histogram comprises a bar for each group (bin) with a non-zero count. Each bar in the radial histogram is rotated by an angle representative of the average angle range of the group (bin) that the bar represents and the length of the bar corresponds to the count for the group (bin) determined in 410.

The radial histogram generated in 412 may then be output and/or alternatively stored (step 414). For example, as part of 414, data encoding the radial histogram may be sent to a renderer that is configured to display the radial histogram on a screen or monitor. The radial histogram may also be printed on a paper using a printer. Various different ways may be used to output the radial histogram. Information encoding the generated radial histogram may also be stored.

Figure 6:
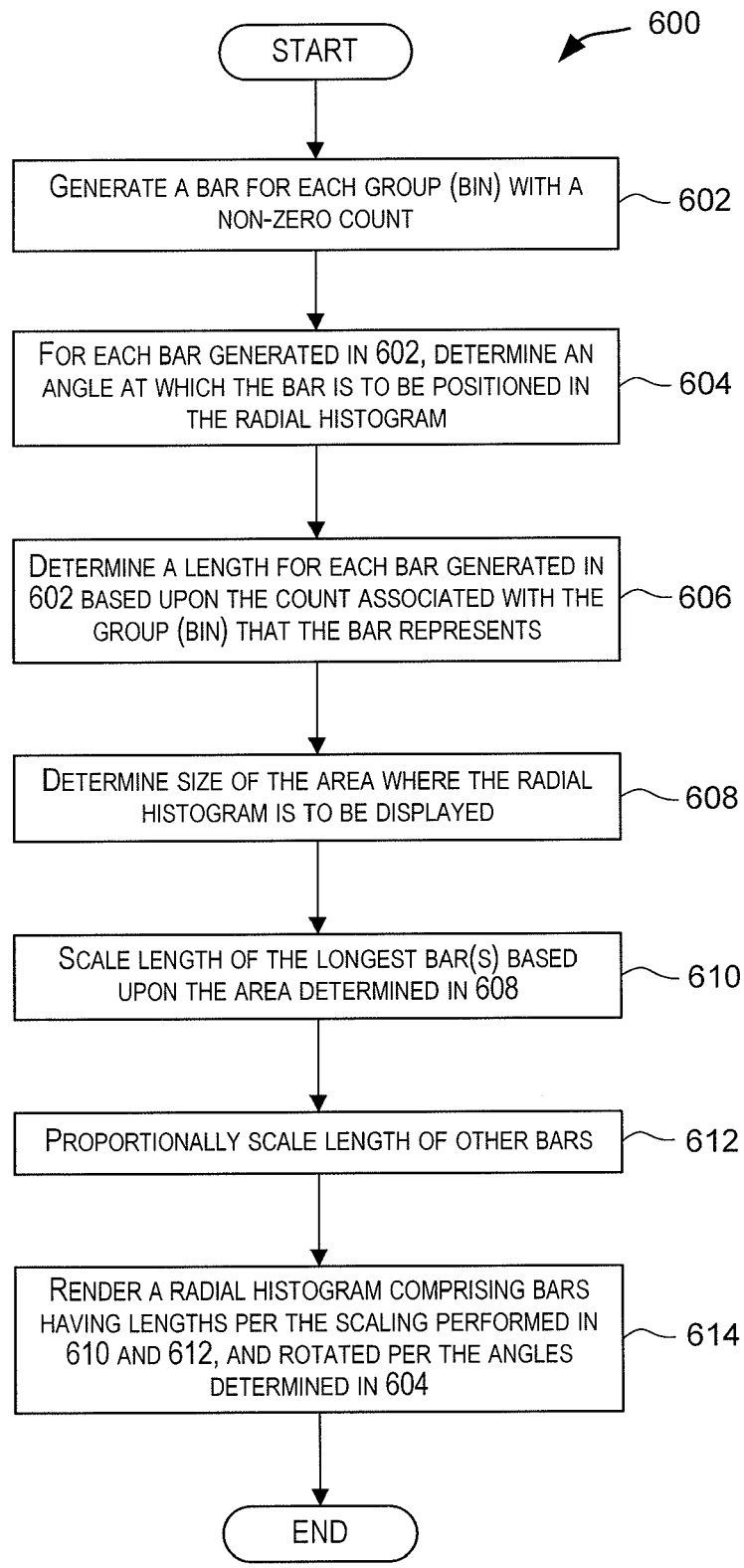
FIG. 6 depicts a high level simplified flowchart depicting a method for rendering a radial histogram according to an embodiment of the present invention.

FIG. 6 depicts a high level simplified flowchart 600 depicting a method for rendering a radial histogram according to an embodiment of the present invention. The method depicted in FIG. 6 may be performed by software (e.g., code, program, and instructions) executed by a processor, in hardware, or combinations thereof. The software may be stored on a computer-readable storage medium. In one embodiment, some of the processing depicted in FIG. 6 may be performed as part of step 412 depicted in FIG. 4 and described above. The method depicted in FIG. 6 is not intended to limit the scope of the application as recited in the claims. In the embodiment depicted in FIG. 2, the processing depicted in FIG. 6 may be performed by path data analyzer 240.

As depicted in FIG. 6, a bar is generated for each group (bin) that has been formed by applying the binning function and that has a non-zero associated count (step 602). For each bar generated in 602, an angle at which the bar is to be rotated and positioned in the radial histogram is then determined (step 604). The angle for a bar is selected such that it is indicative of the angle range of the group (bin) represented by that bar. For example, a bar corresponding to bin {0° to <90°} may be rotated by 0° in the radial histogram, a bar corresponding to bin {90° to <180°} may be rotated by 90°, a bar corresponding to bin {180° to 279°} may be rotated by 180°, a bar corresponding to bin {270° to <360°} may be rotated by 270°. In this embodiment, for a bin, the lower limit of the angle range for the bin is used as the rotation angle.

A length is determined for each bar generated in 602 that is based upon the count associated with the group (bin) represented by the bar (step 606). Accordingly, the group with the highest count has the longest associated bar. The size of the area where the radial histogram is to be displayed is then determined (step 608). In some embodiments, the size of the area may be specified as an input parameter.

The length of the bar with the longest length (as determined in 606) is then scaled based upon the area determined in 608 (step 610). In one embodiment, the scaling is performed such that the radial histogram can be appropriately displayed in the display area. The lengths of all the other bars in the radial histogram are then linearly or proportionately scaled based upon the scaling in 608 (step 612). A radial histogram is then rendered having bars with lengths based upon the processing performed in 610 and 612 and where each bar is rotated and positioned according to the angles determined in 604 (step 614).

Figure 7A:
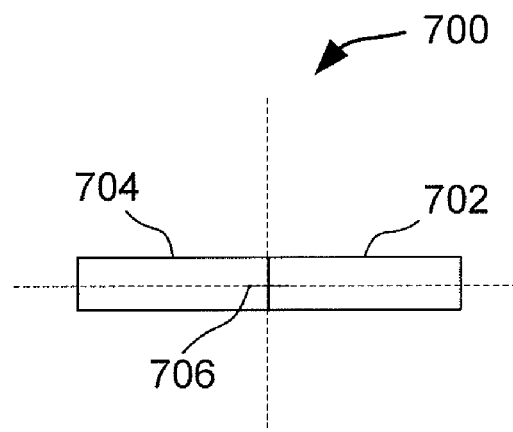
FIG. 7A depicts a radial histogram generated according to an embodiment of the present invention for the path depicted in FIG. 5A using absolute angles.

FIG. 7A depicts a radial histogram 700 generated according to an embodiment of the present invention for path 500 depicted in FIG. 5A using absolute angles. As previously indicated, using absolute angles, the groups (bins) and their counts for path 500 are as follows: {{value: "0° to <90°", count: 2}, {value: "90° to <180°", count: 0}, {value: "180° to <270°", count: 2}, {value: "270° to <360°", count: 0}}. In radial histogram 700, bar 702 represents group {value: "0° to <90°", count: 2} and has been drawn rotated by 0°. Bar 704 represents {value: "180° to <270°", count: 2} and has been drawn rotated by 180°. The length of both the bars is the same corresponding to count 2. Cross 706 marks the center of the bottom edges of the bars about which the bars are rotated. No bars are drawn for bins {value: "90° to <180°"} and {value: "270° to <360°"} since their associated counts are zero.

Figure 7B:
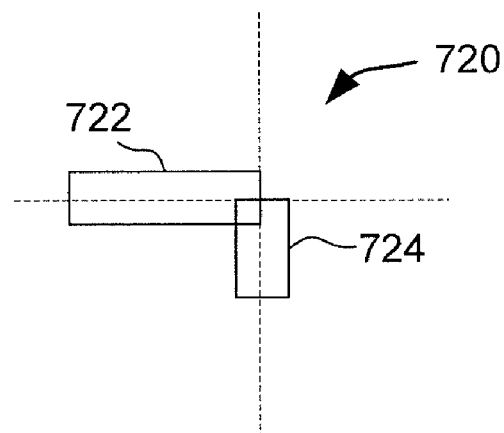
FIG. 7B depicts a radial histogram generated according to an embodiment of the present invention for the path depicted in FIG. 5A using relative angles.

FIG. 7B depicts a radial histogram 720 generated according to an embodiment of the present invention for path 500 depicted in FIG. 5A using relative angles. As previously indicated, using absolute angles RA1, RA2, and RA3 depicted FIG. 5B, the groups (bins) and their counts for path 500 are as follows: {{value: "0° to <90°", count: 0}, {value: "90° to <180°", count: 0}, {value: "180° to <270°", count: 2}, {value: "270° to <360°", count: 1}}. In radial histogram 720, bar 722 represents group {value: "180° to <270°", count: 2} and has been drawn rotated by 180° and has a length corresponding to count 2. Bar 724 represents {value: "270° to <360°", count: 1} and has been drawn rotated by 270° and has a length corresponding to count 1. The length of bar 724 is thus half that of bar 722. As can be seen from FIGS. 7A and 7B, radial histogram 700 generated using absolute angles is different from radial histogram 720 generated using relative angles even though both radial histograms have been generated for the same path.

Figure 17:
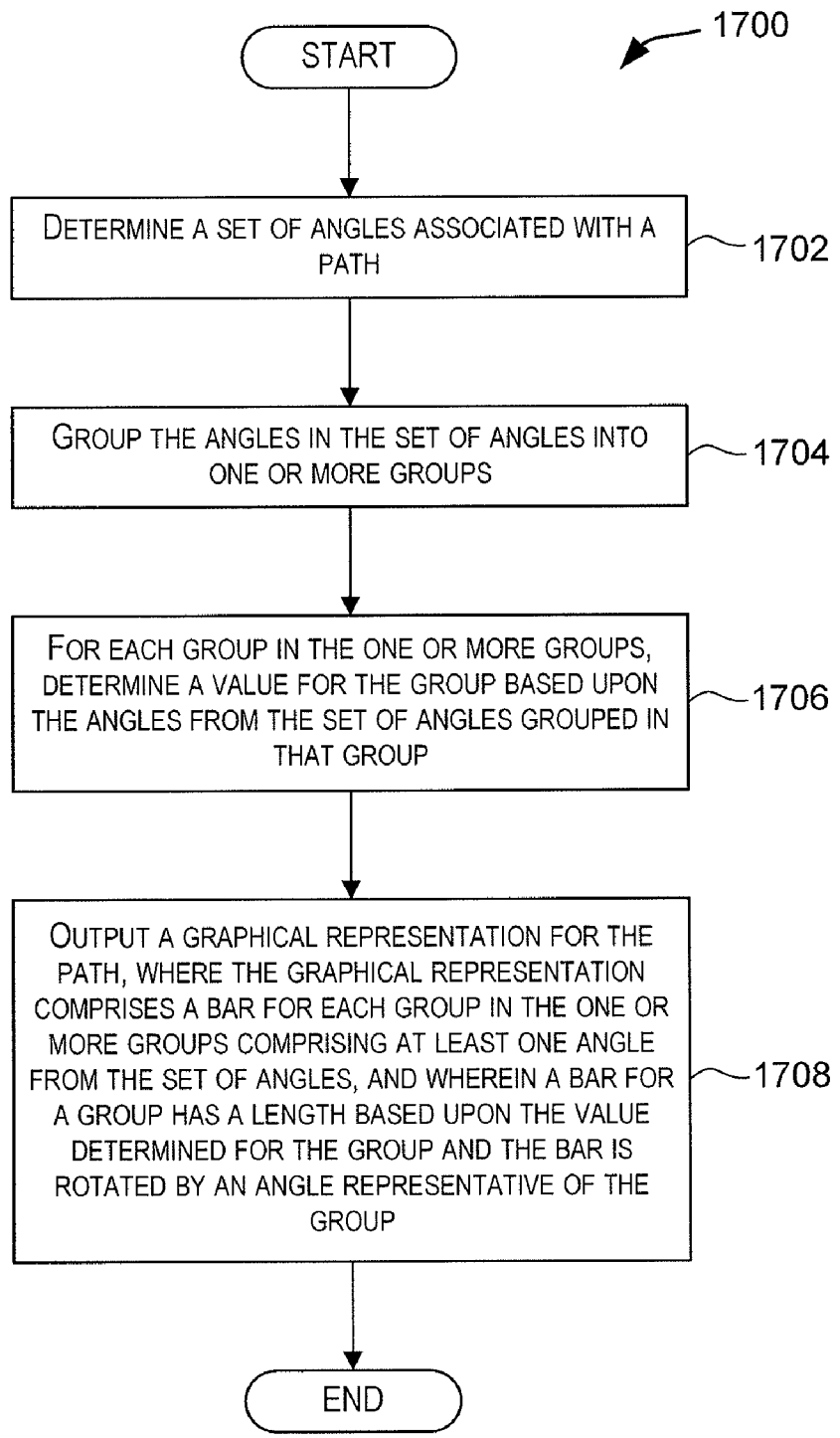
FIG. 17 depicts a high level simplified flowchart depicting a high-level method for rendering a radial histogram according to an embodiment of the present invention.

In the embodiments described above, the count determined for each group is indicative of the number of angles grouped in that group. Zero or more angles may be grouped in a group. A radial histogram is then generated based upon the counts associated with the groups, with the radial histogram comprising a bar for each group with a non-zero count. In alternative embodiments, other functions, besides a count, may be used to determine a value for each group based upon the angles in the group. FIG. 17 depicts a high level simplified flowchart 1700 depicting a high-level method for rendering a radial histogram according to an embodiment of the present invention. The method depicted in FIG. 17 may be performed by software (e.g., code, program, and instructions) executed by a processor, in hardware, or combinations thereof. The software may be stored on a computer-readable storage medium. The method depicted in FIG. 17 is not intended to limit the scope of the application as recited in the claims. In the embodiment depicted in FIG. 2, the processing depicted in FIG. 17 may be performed by path data analyzer 240.

As depicted in FIG. 17, a set of angles associated with a path are determined (step 1702). The angles in the set of angles are then grouped into one or more groups using a grouping/binning function (step 1704). Various different binning functions may be used as described above. A value is then determined for each group in the one or more groups based upon the angles grouped in that group (step 1706). For example, in one embodiment, the value determined for a group may be the number of angles in that group. In alternative embodiments, other techniques or functions may be used to determine a value for a group based upon the angles in the group. For an empty group (i.e., a group with no angles), a zero or null value may be determined. A graphical representation is then output for the path, where the graphical representation comprises a bar for each group in the one or more groups comprising at least one angle from the set of angles (i.e., for each non-empty group), and wherein a bar for a group has a length based upon the value determined for the group and the bar is rotated by an angle representative of the group (step 1708).

As described above, radial histograms may be generated for a path based upon angles associated with the path. The angles for a path may use absolute or relative angles. Since the radial histograms are generated using characteristics of the path (e.g., angles associated with the path), the radial histograms provide a characteristic signature of the path being analyzed. For example, for a scanpath, the shape of a radial histogram generated for the scanpath may indicate an overall scanning strategy used for the scanpath. For example, a radial histogram may indicate whether scanning strategy is primarily multidirectional or unidirectional. Radial histograms calculated with absolute angles may indicate whether a scanning strategy is horizontally-biased or vertically-biased. Radial histograms calculated with relative angles may indicate how a scanning strategy deviates from a trajectory. Radial histograms generated for different scanpaths may be used to compare the different scanpaths.

Aggregate Vector

As described above, as part of generating a radial histogram for a path, a set of angles associated with the path is determined. The angles in the set are then partitioned into groups or bins using a binning function and a count determined for each group or bin. A radial histogram is then generated based upon the counts associated with the groups or bins and the angle ranges represented by the groups or bins. In one embodiment, an aggregate vector (also referred to as a spatial mean indicator) may be used to summarize a radial histogram generated for a path. In one embodiment, in order to determine an aggregate vector for a radial histogram, each bin is considered a vector (a bin vector). For a bin vector, the count associated with the bin is considered as the magnitude of the bin vector and the angle associated with the bin is considered as the angle associated with the bin vector. In one embodiment, the angle associated with a bin is the angle at which a bar representing the bin is rotated by in the radial histogram.

In one embodiment, an aggregate vector for a path may be determined by calculating the average of each of the bin vectors. One method for averaging the bin vectors is to calculate their average angle and their average magnitude. Angles and magnitudes may be averaged directly. In some cases, however, it may be more practical or precise to average the vectors orthogonal components. Given a vector with an angle "a" and a magnitude "m", orthogonal components for the vector may be determined as: $(m*\cos(a))$ and $(m*\sin(a))$. Accordingly, orthogonal components may be determined and averaged for each bin vector. Let X and Y=zero. Let M=the total number of non-zero bins (a "non-zero bin" is a bin with a non-zero count).

For each non-zero bin {

$X=X+(m*\cos(a))/M$ $Y=Y+(m*-\sin(a))/M$

}

The sign of the vertical component is reversed for rendering in a graphics system where positive Y is down.

Then, the aggregate magnitude ("aggregateMagnitude") and aggregate angle ("aggregateAngle") of the aggregate vector for the bin vectors may be determined as:

aggregateMagnitude=square_root($X*X+Y*Y$)

aggregateAngle=−arc_tangent($Y/X$)

An aggregate vector generated in the manner described above may be displayed along with the radial histogram that the aggregate vector summarizes. The aggregateMagnitude represents the length of the aggregate vector measured from an origin point, which is the point representing the center of the bottom edges of the bars in the radial histogram and the point about which the bars are rotated in the radial histogram. The aggregate angle represents the angle at which the aggregate vector is rotated from the reference. In one embodiment, the aggregate vector is displayed by a dot representing the tip of the aggregate vector. The aggregate vector indicates the direction and magnitude of the composite movement of the path represented by the radial histogram.

Figure 8:
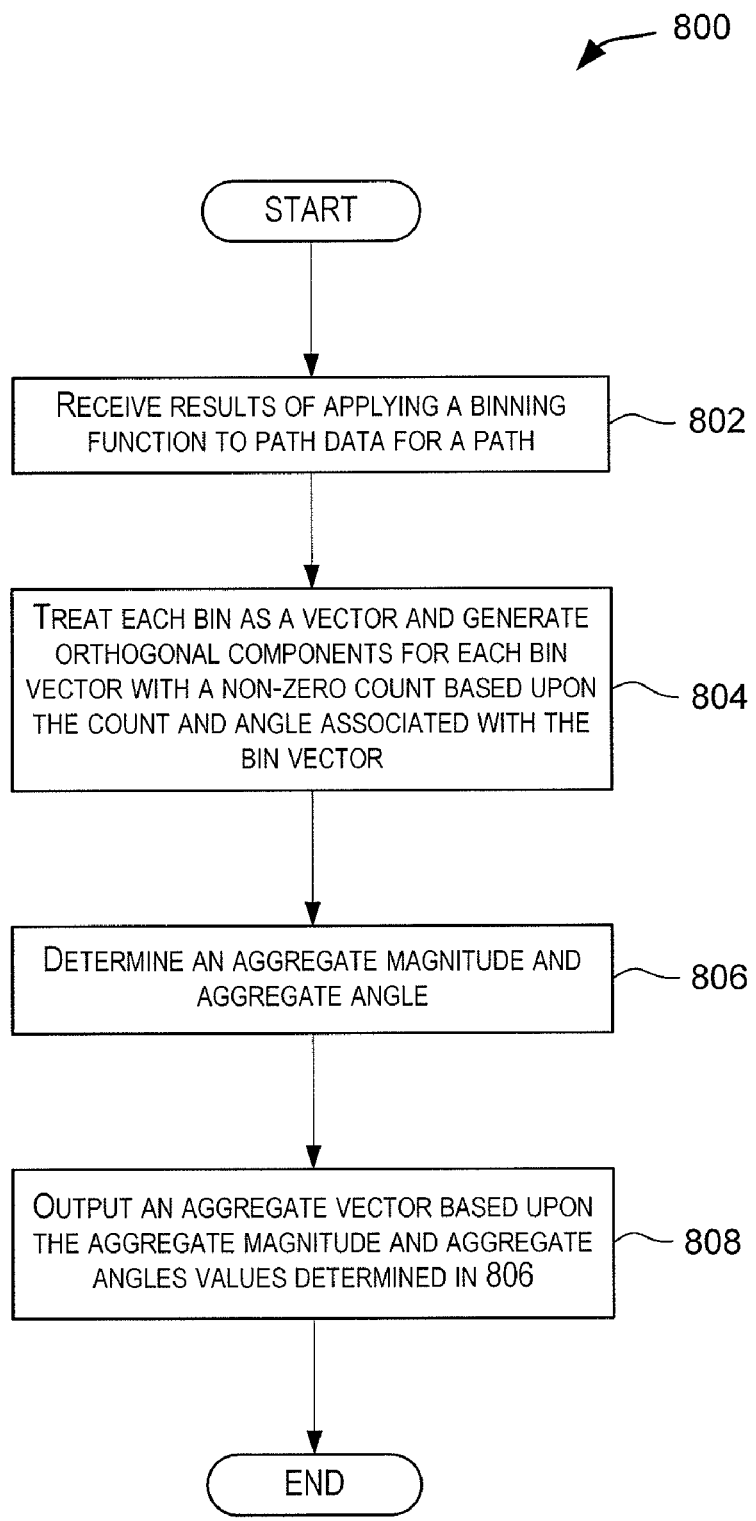
FIG. 8 depicts a simplified high-level flowchart depicting a method for generating an aggregate vector for a radial histogram according to an embodiment of the present invention.

FIG. 8 depicts a simplified high-level flowchart 800 depicting a method for generating an aggregate vector for a radial histogram according to an embodiment of the present invention. The method depicted in FIG. 8 may be performed by path data analyzer 240 in the embodiment depicted in FIG. 2. The method may be implemented in software (e.g., code, program, instructions) executed by a processor, in hardware, or in combinations thereof. The software may be stored on a computer-readable storage medium. The method of FIG. 8 is not intended to limit the scope of the application as recited in the claims.

As depicted in FIG. 8, results of applying a binning function to path data for a path are received (step 802). In one embodiment, the path data for a path comprises a set of angles associated with the path and the binning function is used to partition the angles into subsets or groups of angles. Each bin is then treated as a vector (a bin vector) and orthogonal components are determined for each bin vector with a non-zero magnitude (step 804). The orthogonals for a bin vector are determined based upon a magnitude and angle associated with the bin. In one embodiment, for a bin, the count associated with the bin is treated as the bin vector's magnitude and the angle associated with the bin is treated as the bin vector's angle. In one embodiment, the angle associated with a bin is an angle at which a bar representing the bin is drawn in the radial histogram. Using the magnitude ("m") and angle ("a") for a bin vector, the orthogonals for the bin vector may be determined in one embodiment as: $(m*\cos(a))$ and $(m*\sin(a))$.

An aggregate magnitude and aggregated angle is then determined for the aggregate vector (step 806). In one embodiment, the aggregate magnitude and aggregate angle may be determined as:

M=the total number of non-zero bins

X=summation of each bin vector's$(m*\cos(a))/M$

Y=summation of each bin vector's$(m*-\sin(a))/M$ aggregateMagnitude=square_root($X*X+Y*Y$)

aggregateAngle=−arc_tangent($Y/X$)

An aggregate vector is then output based upon the aggregate magnitude and aggregate angle determined in 806 (step 808). The aggregate vector may be output or rendered along with the radial histogram. The aggregate vector has a length corresponding to aggregateMagnitude and is rotated by an angle corresponding to aggregateAngle. In one embodiment, the aggregate vector is displayed by a dot representing the tip of the aggregate vector.

Figure 9A:
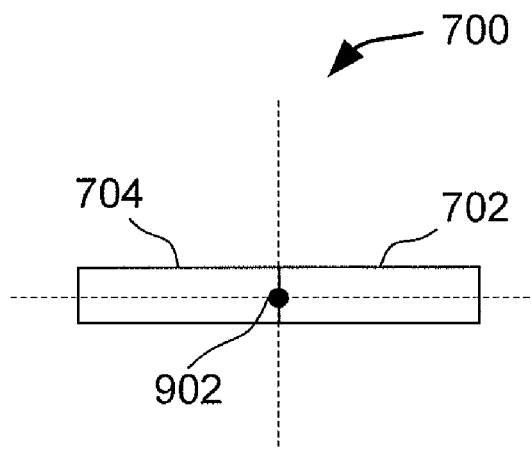
FIG. 9A depicts an aggregate vector and a radial histogram determined for a path based upon absolute angles according to an embodiment of the present invention.

FIG. 9A depicts an aggregate vector and a radial histogram determined for a path based upon absolute angles according to an embodiment of the present invention. FIG. 9A depicts a radial histogram 700 (same as in FIG. 7A) generated for path 500 depicted in FIG. 5A generated based upon absolute angles determined for path 500. Dot 902 represents the aggregate vector generated for the set of absolute angles for path 500. As shown in FIG. 9A, aggregate vector 902 is positioned at the origin.

Figure 9B:
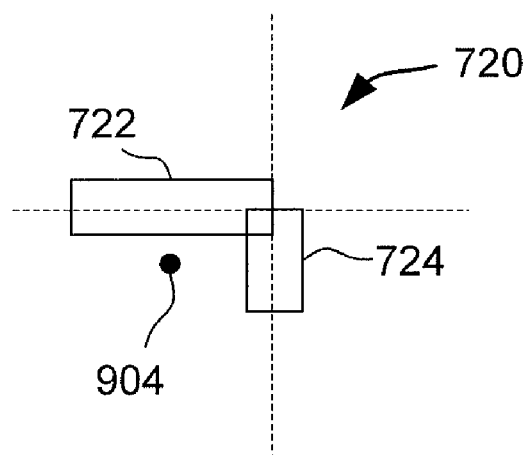
FIG. 9B depicts an aggregate vector and a radial histogram determined for a path based upon relative angles according to an embodiment of the present invention.

FIG. 9B depicts an aggregate vector and a radial histogram determined for a path based upon relative angles according to an embodiment of the present invention. FIG. 9B depicts a radial histogram 720 (same as in FIG. 7B) generated for path 500 depicted in FIG. 5B generated based upon relative angles RA1, RA2, and RA3 determined for path 500. Dot 904 represents the aggregate vector generated for the set of relative angles for path 500.

Radial Vector Plots

The generation of a radial histogram discussed above did not take into account the lengths of the individual path segments in a path. In one embodiment, a graphical representation called a radial vector plot is generated that takes both the angles associated with a path and the lengths of the path segments in the path (e.g., lengths of saccades for a scanpath) into consideration.

Figure 10:
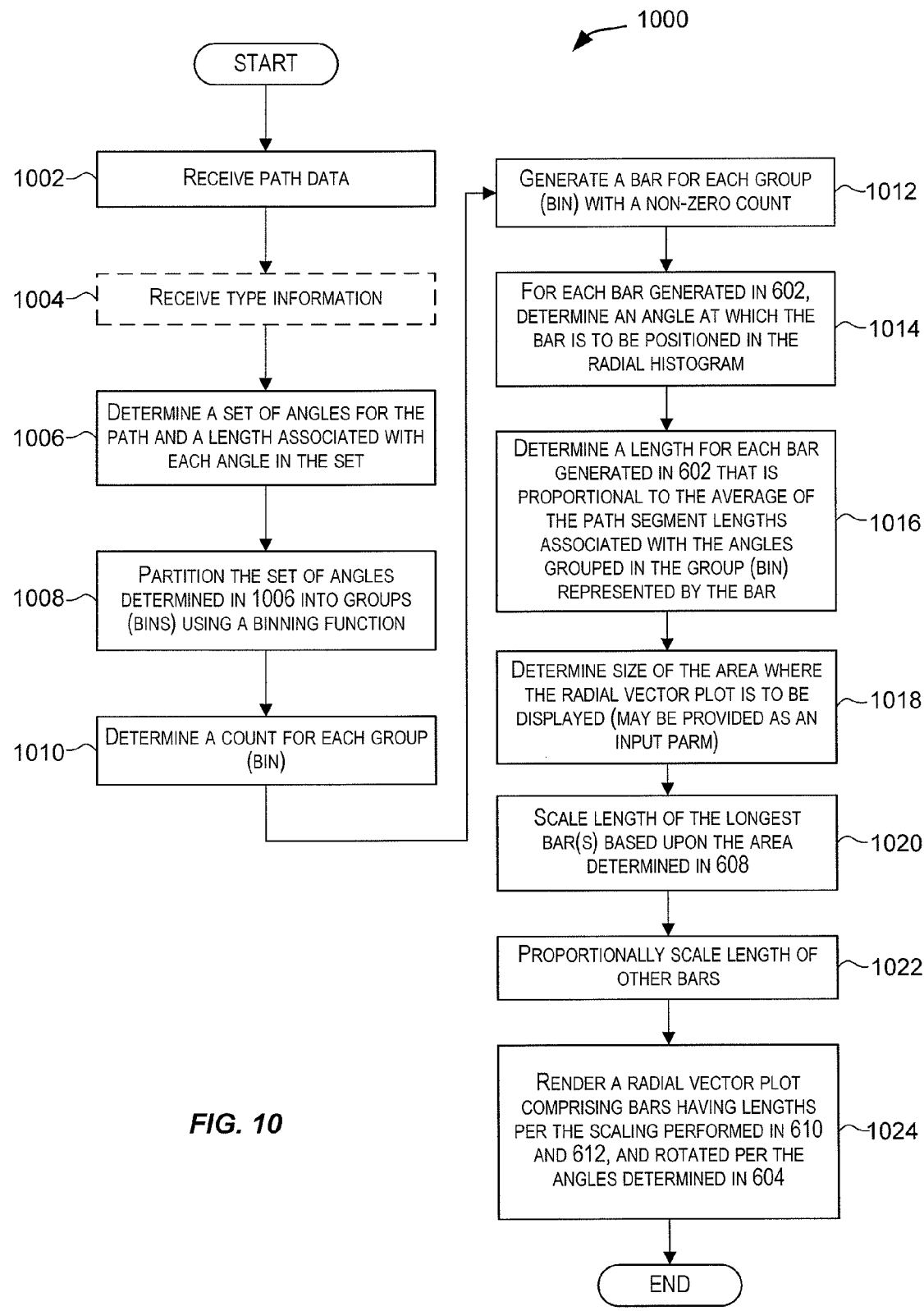
FIG. 10 depicts a high level simplified flowchart depicting a method for generating a radial vector plot according to an embodiment of the present invention.

FIG. 10 depicts a high level simplified flowchart 1000 depicting a method for generating a radial vector plot according to an embodiment of the present invention. The method depicted in FIG. 10 may be performed by software (e.g., code, program, and instructions) executed by a processor, in hardware, or combinations thereof. The software may be stored on a computer-readable storage medium. In one embodiment, the method may be performed by path data analyzer 240 depicted in FIG. 2. The method depicted in FIG. 10 is not intended to limit the scope of the application as recited in the claims.

As depicted in FIG. 10, path data for a path for which a radial vector plot is to be generated is received (step 1002). For example, path data may be received for a scanpath tracking a user's eye movements while viewing a scene. The path data may be received from various sources including from a user via user interface 220, from a device such as an eye tracker, or from another source. In one embodiment, the path data may be stored and retrieved from data store 250. The path data may be received in different formats. For example, the data may be received as data comprising fixation points, transitions between fixation points, etc.

Type information may optionally be received (step 1004). The type information received in 1004 may indicate whether absolute angles or relative angles are to be used for generating the radial vector plot. If no type information is received, then a default method (e.g., using absolute angles) may be used to generate the radial vector plot.

The path data received in 1002 is then analyzed to determine a set of angles associated with the path, and for each angle in the set, a path segment length to be associated with the angle (step 1006). The angles may be measured using either the absolute angle method or the relative angles method.

For example, referring back to FIG. 5A, using an absolute angles method, absolute angles {AA1, AA2, AA3, AA4} may be determined for path 500 defined by the sequence of points {P1, P2, P3, P4, P5}, with P1 being the start point and P5 being the end point of the path. A path segment length is also associated with each angle. In one embodiment, for an absolute angle made by a path segment with an absolute reference, the length of that path segment is determined and associated with the angle. For example, for the path depicted in FIG. 5A, the length of path segment P1P2 is associated with angle AA1, the length of path segment P2P3 is associated with angle AA2, the length of path segment P3P4 is associated with angle AA3, and the length of path segment P4P5 is associated with angle AA4. The angles and associated lengths may be represented as follows: {{AA1, L1}, {AA2, L2}, {AA3, L3}, {AA4, L4}}, where L1 is length of P1P2, L2 is length of P2P3, L3 is length of P3P4, and L4 is length of P4P5.

Using the relative angles method, for the embodiment depicted in FIG. 5B, relative angles {RA1, RA2, RA3} may be determined for path 500. A length is then associated with each of the relative angles. Since relative angles are measured relative to two adjoining paths, there are a number of choices as to what length is associated with a relative angle. In one embodiment, for a relative angle measured between a first path segment and a second path segment, the length of the first path segment (i.e., the path segment, from among the two path segments, that is traversed first while walking the path from the start point to the end point) is associated with the relative angle. For example, for the embodiment depicted in FIG. 5B, the length of path segment P1P2 is associated with angle RA1, the length of path segment P2P3 is associated with angle RA2, and the length of path segment P3P4 is associated with angle RA3. The angles and associated lengths may be represented as follows: {{RA1, L1}, {RA2, L2}, {RA3, L3}}, where L1 is length of P1P2, L2 is length of P2P3, and L3 is length of P3P4.

In another embodiment, for a relative angle measured between a first path segment and a second path segment, the length of the second path segment (i.e., the path segment, from among the two path segments, that is traversed last while walking the path from the start point to the end point) is determined and associated with the relative angle. For example, for the embodiment depicted in FIG. 5B, the length of path segment P2P3 is associated with angle RA1, the length of path segment P3P4 is associated with angle RA2, and the length of path segment P4P5 is associated with angle RA3. The angles and associated lengths may be represented as follows: {{RA1, L1}, {RA2, L2}, {RA3, L3}}, where L1 is length of P2P3, L2 is length of P3P4, and L3 is length of P4P5.

In yet another embodiment, for a relative angle measured between a first path segment and a second path segment, the length that is associated with the angle may be based upon the lengths of the first path segment and the second path segment. For example, in one embodiment, the average of the lengths of the first and second path segments may be determined and associated with the relative angle. For example, for the embodiment depicted in FIG. 5B, the average of the lengths of path segments P1P2 and P2P3 is associated with angle RA1, the average of the lengths of path segments P2P3 and P3P4 is associated with angle RA2, and the average of the lengths of path segments P3P4 and P4P5 is associated with angle RA3. The angles and associated lengths may be represented as follows: {{RA1, L1}, {RA2, L2}, {RA3, L3}}, where L1 is (length(P1P2)+length(P2P3))/2, L2 is (length(P2P3)+length(P3P4))/2, and L3 is (length(P3P4)+length(P4P5))/2. In this embodiment, both the path segments involved in the angle are factored into the length associated with the angle. In another embodiment, the minimum or maximum of the lengths of the first and second path segments may be associated with the angle.

Accordingly, in 1006, a set of angles are determined for the path and a length is associated with each angle in the set of angles. The set of angles (along with their associated lengths) determined in 1006 is then partitioned into groups (or bins) using a binning or grouping function (step 1008). Various different binning functions may be used as previously described such as {{0° to <90°}, {90° to <180°}, {180° to <270°}, {270° to <360°}}. Using the absolute angles example depicted in FIG. 5A, the angles would be binned as follows:
AA1=0°→{0° to <90°} group
AA2=between 180° and <270°→{180° to <270°} group
AA3=180°→{180° to <270°} group
AA4=between 0° and <90°→{0° to <90°} group
Using relative angles RA1, RA2, and RA3 depicted in FIG. 5B, the angles would be binned as follows:
RA1=between 180° and <270°→{180° to <270°} group
RA2=between 270° and <360°→{270° to <360°} group
RA3=between 180° and <270°→{180° to <270°} group After the binning operation in 1008, a count is determined for each group (bin) (step 1010). The count for a group identifies that number of angles (with associated lengths) that are grouped in that group. The groups and respective counts for path 500 depicted in FIG. 5A using absolute angles would be as follows: {{value: "0° to <90°", count: 2}, {value: "90° to <180°", count: 0}, {value: "180° to <270°", count: 2}, {value: "270° to <360°", count: 0}}. Using relative angles RA1, RA2, and RA3 depicted FIG. 5B, the bins and associated counts would be: {{value: "0° to <90°", count: 0}, {value: "90° to <180°", count: 0}, {value: "180° to <270°", count: 2}, {value: "270° to <360°", count: 1}}.

A bar is then generated for each group (bin) that has been formed by applying the binning function and that has a non-zero associated count (step 1012). For each bar generated in 1012, an angle at which the bar is to be rotated and positioned in the radial histogram is then determined (step 1014). The angle for a bar is selected such that it is indicative of the angle range of the group (bin) represented by that bar. For example, a bar corresponding to bin {0° to <90°} may be rotated by 0° in the radial histogram, a bar corresponding to bin {90° to <180°} may be rotated by 90°, a bar corresponding to bin {180° to <270°} may be rotated by 180°, a bar corresponding to bin {270° to <360°} may be rotated by 270°. In this embodiment, for a bin, the lower limit of the angle range for the bin is used as the rotation angle.

A length is determined for each bar generated in 1012 that is proportional to the average of the lengths associated with the angles grouped in the group (bin) represented by the bar (step 1016). For example, using absolute angles, angles {AA1, length of P1P2} and {AA4, length of P4P5} are in the same group {0° to <90°}. In one embodiment, the length of the bar representing this group is proportional to ((length of P1P2)+(length of P4P5))/2.

The size of the area where the radial vector plot is to be displayed is then determined (step 1018). In one embodiment, the area determined in 1018 may be specified by a user as an input parameter. The length of the bar with the longest length (as determined in 1016) is then scaled based upon the area determined in 1018 (step 1020). In one embodiment, the scaling is performed such that the radial vector plot can be appropriately displayed in the display area. The lengths of all the other bars in the radial vector plot are then scaled linearly or proportionately (step 1022). A radial vector plot is then rendered having bars with lengths determined 1020 and 1022 and where each bar is rotated and positioned according to the angle for the bar determined in 1014 (step 1024). As part of 1024, data encoding the radial vector plot may be sent to a renderer that is configured to display the radial vector plot to a user. For example, the radial vector plot may be displayed on a monitor or written as image data into a file. The radial vector plot may also be output in other ways such as being printed on paper using a printer. Various different ways may be used to output the radial vector plot.

In the embodiments described above, a set of angles and path segments associated with a path are determined and a value (e.g., length) is associated with each angle, where the value associated with an angle is based upon the one (for absolute angles) or two (for relative angles) path segments associated with the angle. The angles in the set of angles are then grouped into one or more groups. For each group, a value is then determined based upon the values associated with the angles grouped in that group. Since the value for each angle is determined based upon the path segments associated with that angle, the value for a group is in essence determined based upon the path segments associated with the angles in that group. There are different ways in which a value for a group may be determined based upon the path segments associated with angles that are grouped in that group. One such way is described above for the embodiment depicted in FIG. 10. Other techniques may be used in alternative embodiments wherein the value for a group is determined based upon path segments associated with angles grouped to that group.

Figure 18:
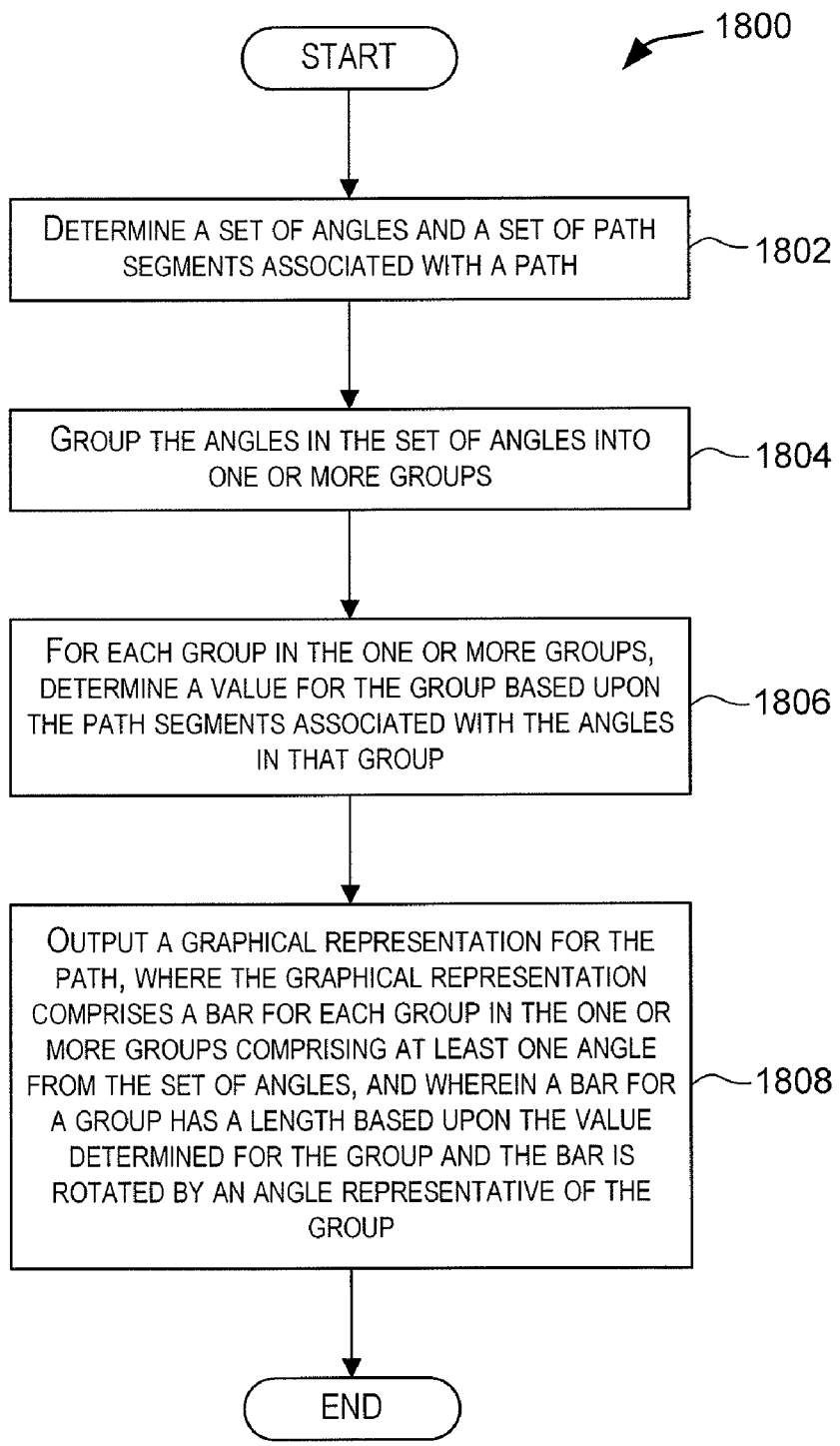
FIG. 18 depicts a high level simplified flowchart depicting a high-level method for rendering a radial vector plot according to an embodiment of the present invention.

FIG. 18 depicts a high level simplified flowchart 1800 depicting a high-level method for rendering a radial vector plot according to an embodiment of the present invention. The method depicted in FIG. 18 may be performed by software (e.g., code, program, and instructions) executed by a processor, in hardware, or combinations thereof. The software may be stored on a computer-readable storage medium. The method depicted in FIG. 18 is not intended to limit the scope of the application as recited in the claims. In the embodiment depicted in FIG. 2, the processing depicted in FIG. 18 may be performed by path data analyzer 240.

As depicted in FIG. 18, a set of path segments and angles associated with a path are determined (step 1802). The angles in the set of angles are then grouped into one or more groups using a grouping/binning function (step 1804). Various different binning functions may be used as described above. A value is then determined for each group in the one or more groups based upon the path segments from the set of path segments associated with the angles grouped in that group (step 1806). In one embodiment, for an angle, the path segments associated with the angle are the path segments that define the angle.

Various different techniques may be used to determine a value for a group based upon the path segments associated with the angles in the group. One such technique has been described above with respect to the embodiment depicted in FIG. 10 wherein the value determined for a group is the average of the path segment lengths associated with the angles grouped in the group. In alternative embodiments, other techniques or functions may be used to determine a value for a group. For example, in one embodiment, for a set of path segments associated with angles in a group, the maximum segment length for the set of path segments may be determined as the value for the group. In another embodiment, the minimum segment length for the set of path segments may be determined as the value for the group. In yet other embodiments, some weighed average of the lengths of the path segments in the set of path segments may be determined as the value for the group. In this manner, the value for a group is determined based upon the path segments associated with angles in the group. For an empty group (i.e., a group with no angles), a zero or null value may be determined.

A graphical representation is then output for the path, where the graphical representation comprises a bar for each group in the one or more groups comprising at least one angle from the set of angles (i.e., for each non-empty group), and wherein a bar for a group has a length based upon the value determined for the group and the bar is rotated by an angle representative of the group (step 1808).

As described above, the bars of the radial vector plot for a path are based both on the angles associated with the path and the lengths of the path segments in the path. This is different from radial histograms that do not take into account the lengths of the path segments in a path. As with radial histograms, an aggregate vector may be determined and displayed for a radial vector plot using the same techniques as described above.

Figure 11A:
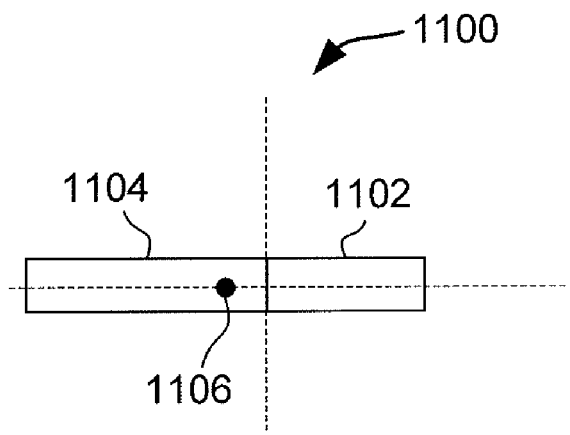
FIG. 11A depicts a radial vector plot and an aggregate vector determined for a path based upon absolute angles according to an embodiment of the present invention.

FIG. 11A depicts a radial vector plot and an aggregate vector determined for a path based upon absolute angles according to an embodiment of the present invention. FIG. 11A depicts a radial vector plot 1100 generated for path 500 depicted in FIG. 5A based upon absolute angles determined for path 500. For purposes of this example, it is assumed that length(P1P2)=length(P3P4)=10 units length(P2P3)=8 units
length(P4P5)=4 units
Accordingly, the absolute angles and their associated lengths are as follows:
{AA1, 10} grouped/binned into {0° to <90°} group
{AA2, 8} grouped/binned into {180° to <270°} group
{AA3, 10} grouped/binned into {180° to <270°} group
{AA4, 4} grouped/binned into {0° to <90°} group
In radial vector plot 1100, bar 1102 represents group {value: "0° to <90°", count: 2} and has been drawn rotated 0°. Bar 1102 has a length that is proportional to the average of the lengths associated with angles AA1 and AA4=average of (Length of path segment P1P2+Length of path segment P4P5)=(10+4)/2=7. Bar 1104 represents {value: "180° to <270°", count: 2} and has been drawn rotated 180°. Bar 1104 has a length that is proportional to the average of the lengths associated with angles AA2 and AA3=average of lengths of path segments P2P3 and P3P4=(8+10)/2=9. Accordingly, the length of bar 1102 is shorter than the length of bar 1104. Dot 1106 represents the aggregate vector generated for the radial vector plot.

Figure 11B:
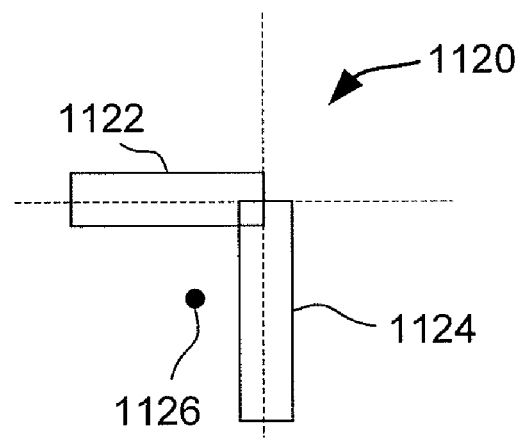
FIG. 11B depicts a radial vector plot and an aggregate vector determined for a path based upon relative angles according to an embodiment of the present invention.

FIG. 11B depicts a radial vector plot and an aggregate vector determined for a path based upon relative angles according to an embodiment of the present invention. FIG. 11B depicts a radial vector plot 1120 generated for path 500 depicted in FIG. 5B generated based upon relative angles RA1, RA2, and RA3 determined for path 500. For the embodiment depicted in FIG. 11B, the length associated with each angle in the set of relative angles is the average of the lengths of the path segments that make the angle.

Accordingly, the relative angles and their associated lengths are as follows:
{RA1, (10+8)/2}={RA1, 9} grouped/binned into {180° to <270°} group
{RA2, (8+10)/2}={RA2, 9} grouped/binned into {270° to <360°} group
{RA3, (10+4)/2}={RA3, 7} grouped/binned into {180° to <270°} group
In radial vector plot 1120, bar 1122 represents group {value: "180° to <270°", count: 2} and has been drawn rotated 180°. Bar 1102 has a length that is proportional to the average of the lengths associated with angles RA1 and RA3=(9+7)/2=8. Bar 1124 represents {value: "270° to <360°", count: 1} and has been drawn rotated 270°. Bar 1124 has a length that is proportional to the length associated with angle RA2 (since angle RA2 is the only member of the group) represented by bar 1124. Accordingly, length of bar 1124 is proportional to 9 (and is thus slightly longer than bar 1122). Dot 1126 represents the aggregate vector generated for the radial vector plot 1120.

Figure 12:
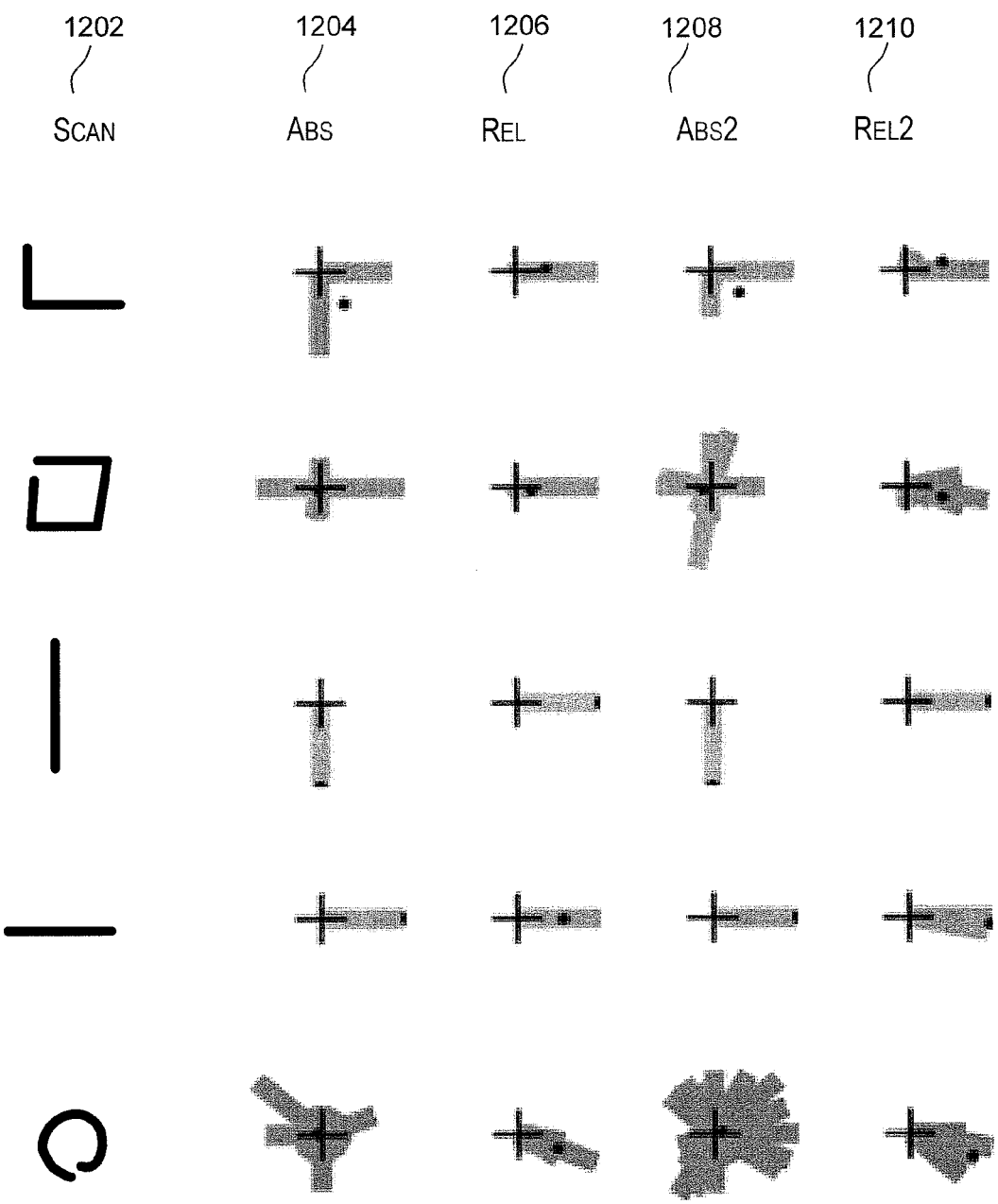
FIG. 12 depicts examples of sample paths and various graphical representations generated for each path according to an embodiment of the present invention.

FIG. 12 depicts examples of sample paths and various graphical representations generated for each path according to an embodiment of the present invention. The sample paths are depicted in column 1202. Each of the paths may have multiple fixation points and path segments. For the embodiments depicted in FIG. 12, a binning function of 10 degrees was used (e.g., {0°-<10°}, {10°-<20°}, etc.). For a path in column 1202: (1) a radial histogram for the path generated using absolute angles is depicted in column 1204; (2) a radial histogram for the path generated using relative angles is depicted in column 1206; (3) a radial vector plot for the path generated using absolute angles is depicted in column 1208; and (4) a radial vector plot for the path generated using relative angles is depicted in column 1210). Aggregate vectors, in the form of dots, are also depicted for each of the graphical representations.

The graphical representations for a path act as signatures for the path since the representations are generated based upon the angles associated with the path and/or the lengths of path segments of the path. A graphical representation thus visually conveys information related to the path. Graphical representations generated for different paths may then be used to compare the paths. The graphical representation thus serves as tools that may be used to analyze and compare paths. For example, the graphical representations may be used for analyzing and comparing scanpaths. For a scanpath, the graphical representations generated for the scanpath convey information about the scanning strategy of the user, such as the general direction in which the user scanned the view, the number of fixations that the user had in any particular direction, etc.

Graphical Representations for Aggregated Paths

In the various embodiments described above (e.g., for radial histograms, radial vector plots, aggregate vectors), a graphical representation is generated for a single path. According to an embodiment, a single graphical representation (such as a radial histogram, radial vector plot, or aggregate vector) may be generated for multiple paths (also referred to as "aggregate paths"). The single graphical representation may also be referred to as an aggregate graphical representation.

Figure 13:
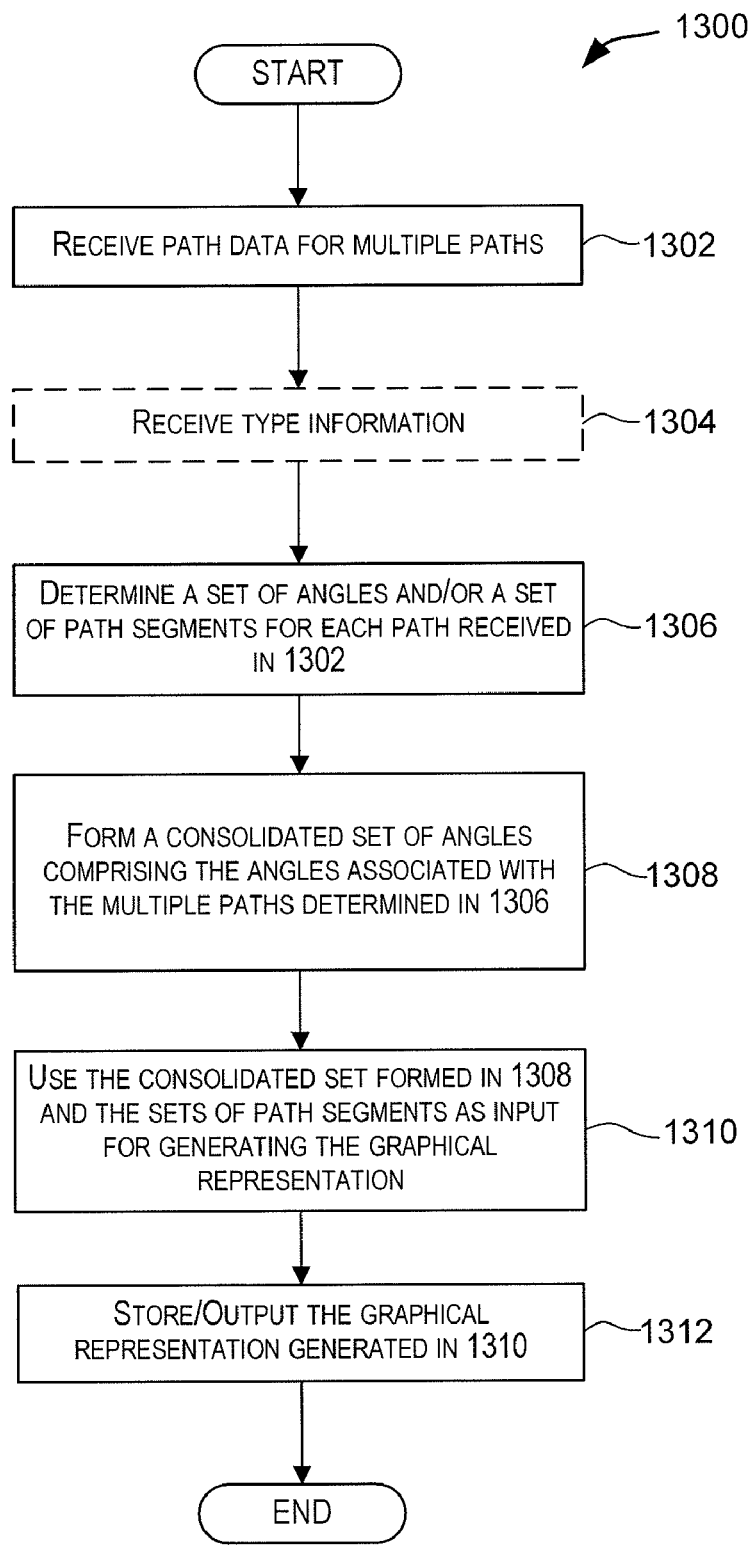
FIG. 13 depicts a high level simplified flowchart depicting a method for generating a graphical representation (referred to as the aggregated graphical representation) for an aggregated path according to an embodiment of the present invention.

FIG. 13 depicts a high level simplified flowchart 1300 depicting a method for generating a graphical representation (referred to as the aggregated graphical representation) for an aggregated path according to an embodiment of the present invention. The method depicted in FIG. 13 may be performed by software (e.g., code, program, and instructions) executed by a processor, in hardware, or combinations thereof. The software may be stored on a computer-readable storage medium. In one embodiment, the method may be performed by path data analyzer 240 depicted in FIG. 2. The method depicted in FIG. 13 is not intended to limit the scope of the application as recited in the claims.

As depicted in FIG. 13, path data may be received for multiple paths to be aggregated (step 1302). For example, the data may be received for multiple scanpaths that are to be aggregated. Type information may optionally be received (step 1304) indicating whether absolute angles or relative angles are to be used for generating the aggregated graphical representation.

A set of angles and/or a set of path segments may be then determined for each of the paths for which data is received in 1302 (step 1306). A consolidated set of angles is then formed comprising the angles associated with the multiple paths determined in 1306 (step 1308). The consolidated set of angles and the sets of path segments are then used as input to generate the aggregated graphical representation (step 1310). For example, if an aggregate radial histogram is to be generated, the processing depicted in FIG. 17 and/or FIGS. 4 and 6, as described above, may be applied to the consolidated set of angles to generate an aggregate radial histogram. If an aggregate radial vector plot is to be generated, then the consolidated set of angles may be used as an input sequence to the binning function according to step 1008 depicted in FIG. 10. If an aggregate radial vector plot is to be generated, the processing depicted in FIG. 18 and/or FIG. 10, as described above, may be applied to the consolidated set of angles and associated path segments to generate an aggregated radial vector plot. The processing depicted in FIG. 8 may be used to determine an aggregate vector for the aggregate graphical representation (either for an aggregate radial histogram or an aggregate radial vector plot). An aggregated graphical representation generated in 1310 may then be output (step 1312).

Figure 14:
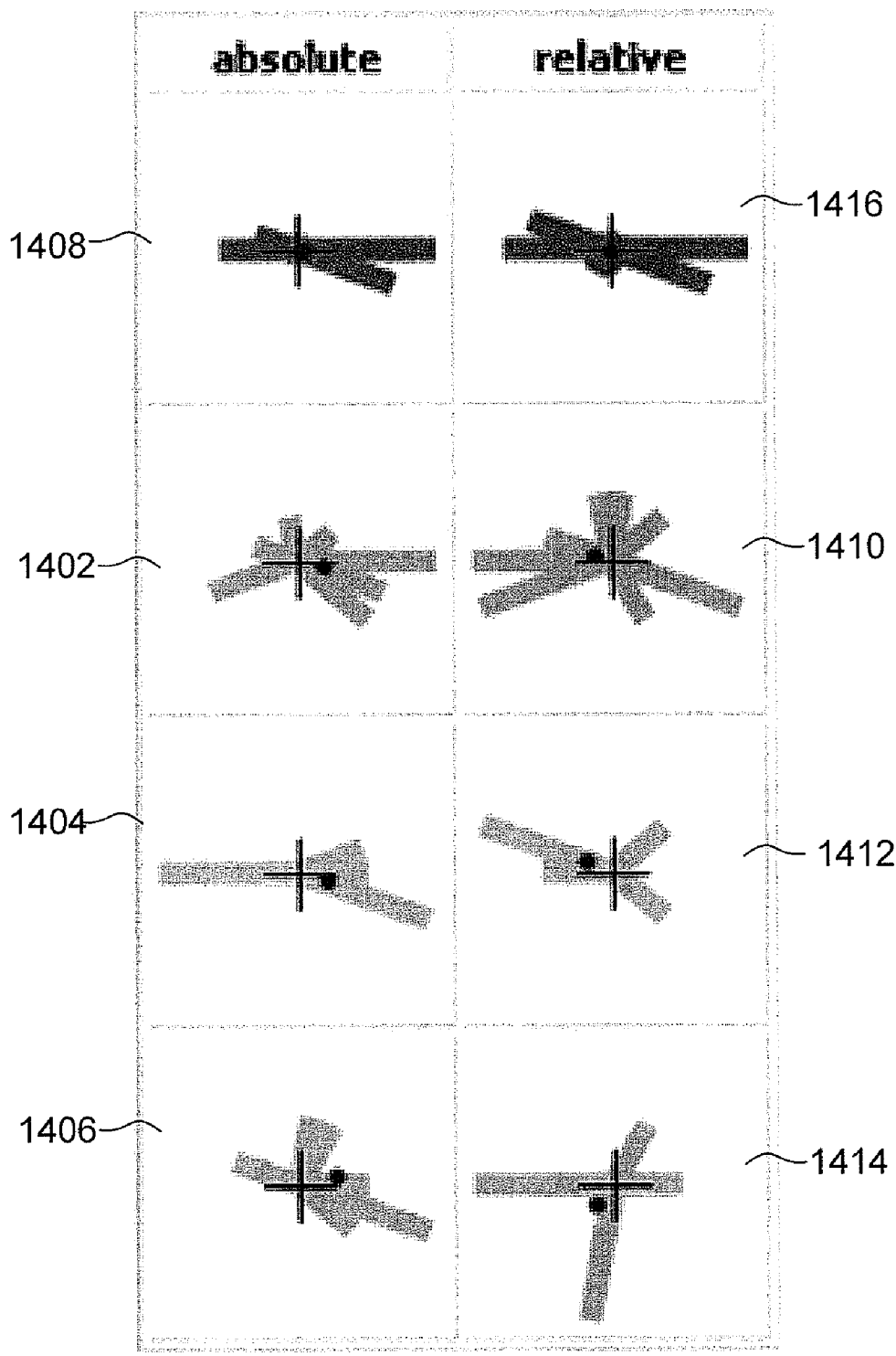
FIG. 14 depicts examples of aggregated graphical representations generated according to an embodiment of the present invention.

FIG. 14 depicts examples of aggregated graphical representations generated according to an embodiment of the present invention. In FIG. 14, graphical representations 1402, 1404, and 1406 are generated for three paths respectively using absolute angles. Graphical representations 1410, 1412, and 1414 are generated for same three paths respectively using relative angles. Graphical representation 1408 represents the aggregated graphical representation (using absolute angles) generated for the three paths aggregated together. Graphical representation 1416 represents the aggregated graphical representation (using relative angles) generated for the same three paths aggregated together. Aggregate vectors are also depicted for the each of the graphical representations in the form of dots.

In the various embodiments described above, binning is used to partition the set of angles associated with a path (or aggregated path) into groups or bins. In one embodiment, hashtables may be used to facilitate binning because they are useful for detecting duplicate values. When binning, it is useful to be able to tell if a given input, a binned angle in this case, has already been indexed or not. For computing radial histograms, each path angle may be binned and the bin angle used as a key into an initially empty hashtable. If the key is not in the hashtable, a new entry is added to the hash table using the binned angle as the key and 1 as the value. If the key is already in the hashtable, the value associated with the key is incremented. For radial vector plots, instead of associating just the count with each bin, an array of lengths may be stored in the hashtable. These lengths can then be averaged to calculate the radial plot. Hashtables are however not the only data structure that is useful for detecting duplicate values and that may be used for binning In JavaScript, for example, or other property-based object-oriented languages, an object's property system may be used. In such a system, the 'property name' is like the "key" and the 'property value' is like the value. So binned angles may be used as property names for an initially empty object. If the object does not have a property with the name of the binned angle, it is given a new property with the name of the binned angle and a value of 1. If the object already has a property with the name of the binned angle, the property's value is incremented.

Figure 15:
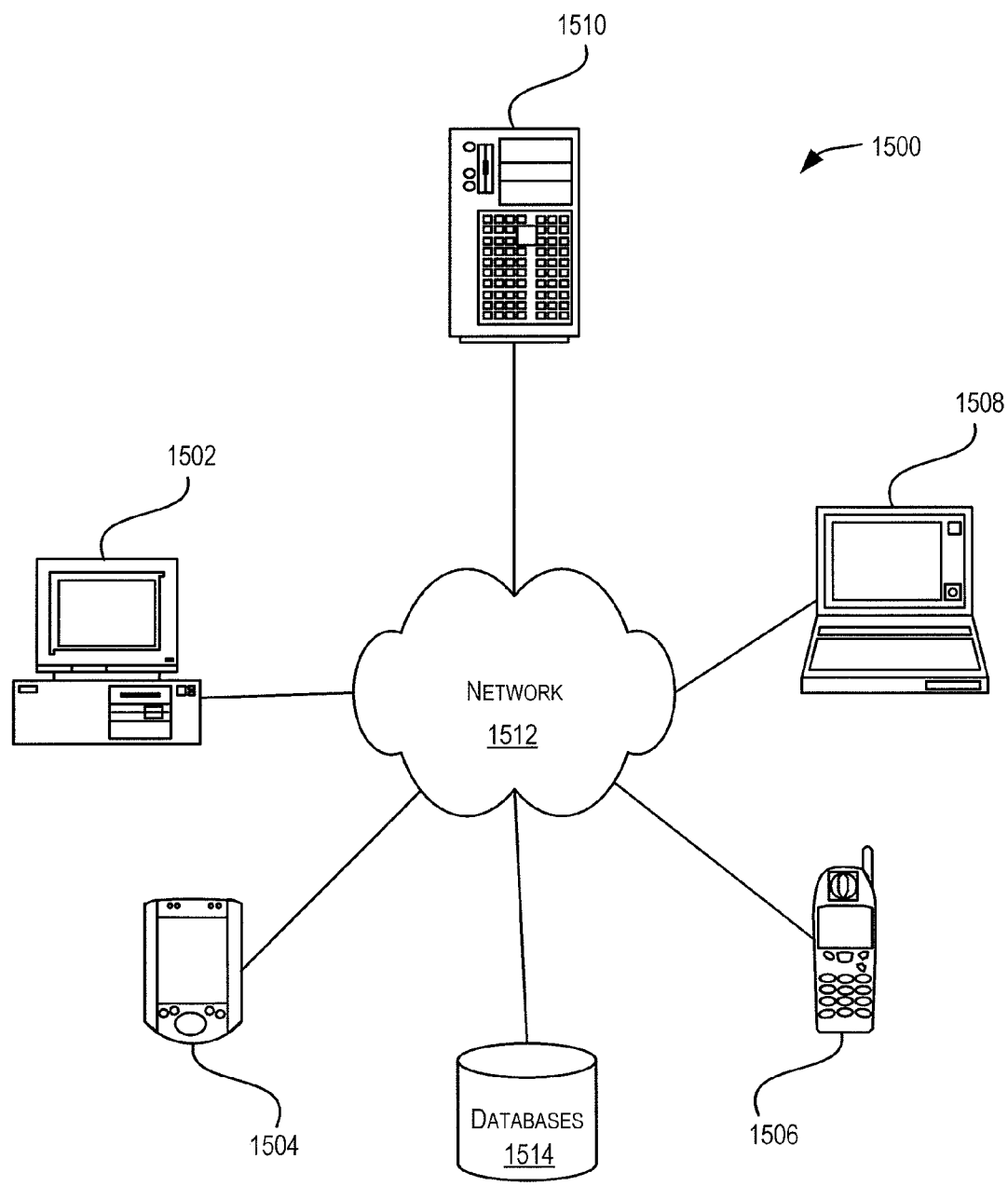
FIG. 15 is a simplified block diagram illustrating a system environment that may be used in accordance with an embodiment of the present invention.

FIG. 15 is a simplified block diagram illustrating a system environment 1500 that may be used in accordance with an embodiment of the present invention. As shown, system environment 1500 includes one or more client computing devices 1502, 1504, 1506, 1508 communicatively coupled with a server computer 1510 via a network 1512. In one set of embodiments, server computer 1510 may be configured as per data processing system 200 depicted in FIG. 2. Client computing devices 1502, 1504, 1506, 1508 may be configured to run one or more client applications that interact with server 1510. Although system environment 1500 is shown with four client computing devices and one server computer, any number of client computing devices and server computers may be supported.

Client computing devices 1502, 1504, 1506, 1508 may be general purpose personal computers (including, for example, personal computers and/or laptop computers running various versions of Microsoft Windows and/or Apple Macintosh operating systems), cell phones or PDAs (running software such as Microsoft Windows Mobile and being Internet, e-mail, SMS, Blackberry, and/or other communication protocol enabled), and/or workstation computers running any of a variety of commercially-available UNIX or UNIX-like operating systems (including without limitation the variety of GNU/Linux operating systems). Alternatively, client computing devices 1502, 1504, 1506, 1508 may be any other electronic device capable of communicating over a network (e.g., network 1512 described below) with server computer 1510.

Server computer 1510 may be a general purpose computer, specialized server computer (including, e.g., a LINUX server, UNIX server, mid-range server, mainframe computer, rack-mounted server, etc.), server farm, server cluster, or any other appropriate arrangement and/or combination. Server computer 1510 may run an operating system including any of those discussed above, as well as any commercially available server operating system. Server computer 1510 may also run any of a variety of server applications and/or mid-tier applications, including web servers, Java virtual machines, application servers, database servers, and the like. As indicated above, in one set of embodiments, server computer 1510 is adapted to generate graphical representations for one or more paths as described above.

As shown, client computing devices 1502, 1504, 1506, 1508 and server computer 1510 are communicatively coupled via network 1512. Network 1512 may be any type of network that can support data communications using any of a variety of commercially-available protocols, including without limitation TCP/IP, SNA, IPX, AppleTalk, and the like. Merely by way of example, network 1512 may be a local area network (LAN), such as an Ethernet network, a Token-Ring network and/or the like; a wide-area network; a virtual network, including without limitation a virtual private network (VPN); the Internet; an intranet; an extranet; a public switched telephone network (PSTN); an infra-red network; a wireless network (e.g., a network operating under any of the IEEE 802.11 suite of protocols, the Bluetooth protocol known in the art, and/or any other wireless protocol); and/or any combination of these and/or other networks.

System environment 1500 may also include one or more databases 1514. In one set of embodiments, database 1514 can include any other database or data storage components that store data that is used for generating graphical representations for paths as discussed above. For example, database 1514 may store eye tracking data, scanpath data, data representing graphical representations, and the like. Database 1514 may reside in a variety of locations. By way of example, database 1514 may reside on a storage medium local to (and/or resident in) one or more of the computers 1502, 1504, 1506, 1508, 1510. Alternatively, database 1514 may be remote from any or all of the computers 1502, 1504, 1506, 1508, 1510 and/or in communication (e.g., via network 1512) with one or more of these. In one set of embodiments, database 1514 may reside in a storage-area network (SAN) familiar to those skilled in the art. Similarly, any necessary files for performing the functions attributed to the computers 1502, 1504, 1506, 1508, 1510 may be stored locally on the respective computer and/or remotely on database 1514, as appropriate. In one set of embodiments, database 1514 is a relational database, such as an Oracle database (e.g., Oracle 10g) available from Oracle Corporation.

Figure 16:
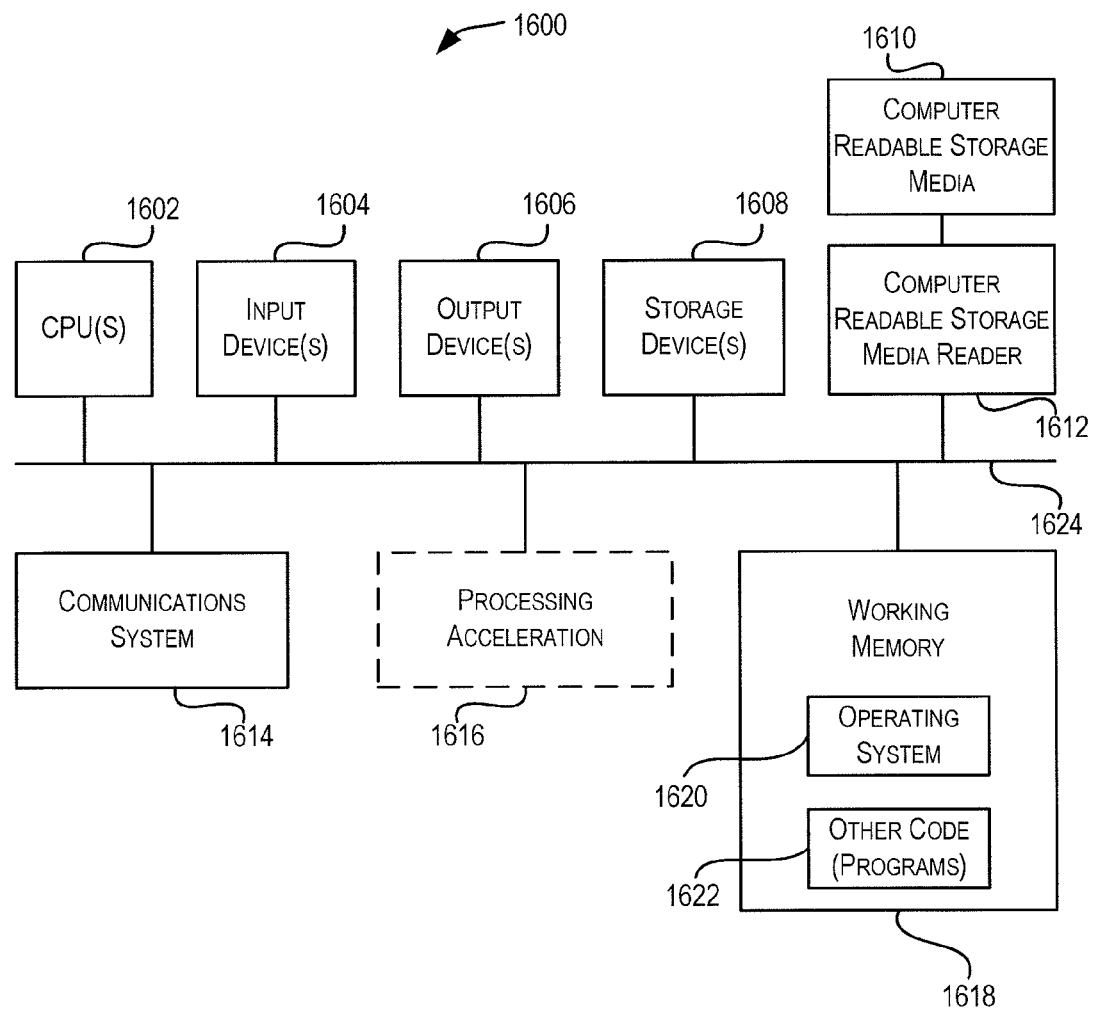
FIG. 16 is a simplified block diagram illustrating physical components of a computer system that may incorporate an embodiment of the present invention.

FIG. 16 is a simplified block diagram illustrating physical components of a computer system 1600 that may incorporate an embodiment of the present invention. In various embodiments, computer system 1600 may be used to implement any of the computers 1502, 1504, 1506, 1508, 1510 illustrated in system environment 1500 described above. As shown in FIG. 16, computer system 1600 comprises hardware elements that may be electrically coupled via a bus 1624. The hardware elements may include one or more central processing units (CPUs) 1602, one or more input devices 1604 (e.g., a mouse, a keyboard, etc.), and one or more output devices 1606 (e.g., a display device, a printer, etc.). Computer system 1600 may also include one or more storage devices 1608. By way of example, storage device(s) 1608 may include devices such as disk drives, optical storage devices, and solid-state storage devices such as a random access memory (RAM) and/or a read-only memory (ROM), which can be programmable, flash-updateable and/or the like.

Computer system 1600 may additionally include a computer-readable storage media reader 1612, a communications subsystem 1614 (e.g., a modem, a network card (wireless or wired), an infra-red communication device, etc.), and working memory 1618, which may include RAM and ROM devices as described above. In some embodiments, computer system 1600 may also include a processing acceleration unit 1616, which can include a digital signal processor (DSP), a special-purpose processor, and/or the like.

Computer-readable storage media reader 1612 can further be connected to a computer-readable storage medium 1610, together (and, optionally, in combination with storage device(s) 1608) comprehensively representing remote, local, fixed, and/or removable storage devices plus storage media for temporarily and/or more permanently containing computer-readable information. Communications system 1614 may permit data to be exchanged with network 1512 of FIG. 15 and/or any other computer described above with respect to system environment 1500.

Computer system 1600 may also comprise software elements, shown as being currently located within working memory 1618, including an operating system 1620 and/or other code 1622, such as an application program (which may be a client application, Web browser, mid-tier application, RDBMS, etc.). It should be appreciated that alternative embodiments of computer system 1600 may have numerous variations from that described above. For example, customized hardware might also be used and/or particular elements might be implemented in hardware, software (including portable software, such as applets), or both. Further, connection to other computing devices such as network input/output devices may be employed.

In one set of embodiments, the techniques described herein may be implemented as program code executable by a computer system (such as a computer system 1600) and may be stored on machine-readable storage media. Machine-readable storage media may include any appropriate media known or used in the art, including storage media and communication media, such as (but not limited to) volatile and non-volatile, removable and non-removable media implemented in any method or technology for storage and/or transmission of information such as machine-readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, or any other medium which can be used to store or transmit the desired information and which can be accessed by a computer.

Although specific embodiments of the invention have been described, various modifications, alterations, alternative constructions, and equivalents are also encompassed within the scope of the invention. Embodiments of the present invention are not restricted to operation within certain specific data processing environments, but are free to operate within a plurality of data processing environments. Additionally, although embodiments of the present invention have been described using a particular series of transactions and steps, it should be apparent to those skilled in the art that the scope of the present invention is not limited to the described series of transactions and steps.

Further, while embodiments of the present invention have been described using a particular combination of hardware and software, it should be recognized that other combinations of hardware and software are also within the scope of the present invention. Embodiments of the present invention may be implemented only in hardware, or only in software, or using combinations thereof.

The specification and drawings are, accordingly, to be regarded in an illustrative rather than a restrictive sense. It will, however, be evident that additions, subtractions, deletions, and other modifications and changes may be made thereunto without departing from the broader spirit and scope as set forth in the claims.

What is claimed is:

1. A computer-readable storage device storing a plurality of instructions which, when executed by a processor, cause the processor to display a graphical representation for a path by:
    determining a set of angles associated with the path;
    grouping the angles in the set of angles into a set of one or more groups;
    determining a value for each group in the set of groups based upon the angles from the set of angles that are grouped in that group; and
    outputting a radial histogram as a graphical representation for the path, the radial histogram comprising a bar for each group in the set of groups, wherein the bar for each group has a length based upon the value determined for the group and wherein the bar for each group has a position rotated from an origin by an average angle representative of the group.

2. The computer-readable storage device of claim 1, wherein the value determined for each group in the set of groups is indicative of a number of angles from the set of angles that are grouped in that group.

3. The computer-readable storage device of claim 1, wherein:
    the path comprises one or more path segments; and
    determining the set of angles comprises determining an angle each path segment makes with respect to a common absolute reference.

4. The computer-readable storage device of claim 1, wherein:
    the path comprises one or more path segments; and
    determining the set of angles comprises, for each pair of adjoining path segments in the path, determining an angle between the path segments in the pair.

5. The computer-readable storage device of claim 1, further comprising:
    determining an average magnitude, wherein the average magnitude is equal to the average of the values determined for one or more groups in the set of groups comprising at least one angle from the set of angles;
    determining an average angle, wherein the average angle is equal to the average of the angles representative of the one or more groups in the set of groups comprising at least one angle from the set of angles; and
    outputting a second graphical representation based upon the aggregate magnitude and the aggregate angle.

6. The computer-readable storage device of claim 1, further comprising:
    for each group in the set of groups comprising at least one angle from the set of angles, determining a first orthogonal and a second orthogonal for the group based upon the value determined for the group and the angle representative of the group;

determining an aggregate magnitude based upon the first and second orthogonals determined for the set of groups;

determining an aggregate angle based upon the first and second orthogonals determined for the set of groups; and outputting a second graphical representation based upon the aggregate magnitude and the aggregate angle.

7. The computer-readable storage device of claim 1, further comprising:

for each group in the set of groups comprising at least one angle from the set of angles:

determining a length for the bar for the group based upon the value determined for the group; and determining an angle representative of the group.

8. The computer-readable storage device of claim 7, further comprising:

for each group in the set of groups comprising at least one angle from the set of angles, scaling the length of the bar for the group based upon an area available for outputting the graphical representation; and wherein outputting the graphical representation comprises, for each group in the set of groups comprising at least one angle from the set of angles, displaying the scaled bar for the group in the graphical representation.

9. The computer-readable storage device of claim 1, wherein the path is a scanpath representing a path followed by an eye when viewing a scene.

10. A system for displaying information related to a path, the system comprising:

a display; and a processor;

wherein the processor is configured to:

determine a set of angles associated with the path;

group the angles in the set of angles into a set of one or more groups;

determine a value for each group in the set of groups based upon the angles from the set of angles that are grouped in that group; and output a radial histogram as a graphical representation for the path, the radial histogram comprising a bar for each group in the set of groups, wherein the bar for each group has a length based upon the value determined for the group and wherein the bar for each group has a position rotated from an origin by an average angle representative of the group.

11. The system of claim 10 wherein the value determined for each group in the set of groups is indicative of a number of angles from the set of angles that are grouped in that group.

12. The system of claim 10 wherein:

the path comprises one or more path segments; and the processor is configured to determine an angle each path segment makes with respect to a common absolute reference.

13. The system of claim 10 wherein:

the path comprises one or more path segments; and the processor is configured to, for each pair of adjoining path segments in the path, determine an angle between the path segments in the pair.

14. The system of claim 10 wherein the processor is further configured to:

determine an average magnitude, wherein the average magnitude is equal to the average of the values determined for one or more groups in the set of groups comprising at least one angle from the set of angles;

determine an average angle, wherein the average angle is equal to the average of the angles representative of the one or more groups in the set of groups comprising at least one angle from the set of angles; and output a second graphical representation based upon the aggregate magnitude and the aggregate angle.

15. The system of claim 10 wherein the processor is further configured to:

for each group in the set of groups comprising at least one angle from the set of angles, determine a first orthogonal and a second orthogonal for the group based upon the value determined for the group and the angle representative of the group;

determine an aggregate magnitude based upon the first and second orthogonals determined for the set of groups;

determine an aggregate angle based upon the first and second orthogonals determined for the set of groups; and output a second graphical representation based upon the aggregate magnitude and the aggregate angle.

16. The system of claim 10 wherein the processor is further configured to:

for each group in the set of groups comprising at least one angle from the set of angles:

determine a length for the bar for the group based upon the value determined for the group; and determine an angle representative of the group.

17. The system of claim 16 wherein the processor is configured to:

for each group in the set of groups comprising at least one angle from the set of angles, scale the length of the bar for the group based upon an area available for outputting the graphical representation; and display the scaled bar in the graphical representation.

18. The system of claim 10 wherein the path is a scanpath representing a path followed by an eye when viewing a scene.

19. A computer-implemented method for displaying a graphical representation for a path, the method:

determining, by a processing system, a set of angles associated with the path;

grouping, by the processing system, the angles in the set of angles into a set of one or more groups;

determining, by the processing system, a value for each group in the set of groups based upon the angles from the set of angles that are grouped in that group; and outputting, by the processing system, a radial histogram as a graphical representation for the path, the graphical representation radial histogram comprising a bar for each group in the set of groups, wherein the bar for each group has a length based upon the value determined for the group and wherein the bar for each group has a position rotated from an origin by an average angle representative of the group.

20. The method of claim 19 wherein the value determined for each group in the set of groups is indicative of a number of angles from the set of angles that are grouped in that group.

* * * * *

UNITED STATES PATENT AND TRADEMARK OFFICE
CERTIFICATE OF CORRECTION

| | | |
|---|---|---|
| PATENT NO. | : 8,390,626 B2 | Page 1 of 1 |
| APPLICATION NO. | : 12/616016 | |
| DATED | : March 5, 2013 | |
| INVENTOR(S) | : Helfman et al. | |

It is certified that error appears in the above-identified patent and that said Letters Patent is hereby corrected as shown below:

On title page 3, in column 1, under "Other Publications", line 6, delete "www.journalof vision.org" and insert -- www.journalofvision.org --, therefor.

In the Specification:

In column 5, line 5, delete "maybe" and insert -- may be --, therefor.

In column 21, line 32, delete "binning" and insert -- binning. --, therefor.

In the Claims:

In column 26, line 50-51, in Claim 19, after "path, the" delete "graphical representation".

Signed and Sealed this
Second Day of July, 2013

Teresa Stanek Rea
*Acting Director of the United States Patent and Trademark Office*